US008269215B2

(12) United States Patent
Katz et al.

(10) Patent No.: US 8,269,215 B2

(45) Date of Patent: Sep. 18, 2012

(54) PYROMELLITIC DIIMIDE ORGANIC SEMICONDUCTORS AND DEVICES

(75) Inventors: Howard Edan Katz, Owings Mill, MD (US); Qingdong Zheng, Baltimore, MD (US); Byung Jun Jung, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 12/999,733

(22) PCT Filed: Jul. 21, 2009

(86) PCT No.: PCT/US2009/051265

§ 371 (c)(1), (2), (4) Date: Dec. 17, 2010

(87) PCT Pub. No.: WO2010/011658

PCT Pub. Date: Jan. 28, 2010

(65) Prior Publication Data

US 2011/0163301 A1 Jul. 7, 2011

Related U.S. Application Data

(60) Provisional application No. 61/082,284, filed on Jul. 21, 2008, provisional application No. 61/082,339, filed on Jul. 21, 2008.

(51) Int. Cl.

| | |
|---|---|
| ***H01L 51/54*** | (2006.01) |
| ***H01L 51/30*** | (2006.01) |
| ***C07D 487/04*** | (2006.01) |

(52) U.S. Cl. ..................... 257/40; 548/433; 257/E51.05

(58) Field of Classification Search .................... 257/40, 257/E51.05; 548/433

See application file for complete search history.

(56) References Cited

U.S. PATENT DOCUMENTS

| | | | | |
|---|---|---|---|---|
| 5,976,208 | A | 11/1999 | Rousseau et al. | |
| 2007/0111371 | A1 | 5/2007 | Ahn et al. | |
| 2007/0160905 | A1 | 7/2007 | Morishita et al. | |
| 2008/0061288 | A1 | 3/2008 | Tomono et al. | |
| 2009/0072224 | A1* | 3/2009 | Aramaki et al. | 257/40 |

FOREIGN PATENT DOCUMENTS

| | | | |
|---|---|---|---|
| EP | 0010440 | A1 | 4/1980 |
| JP | 4-328121 | A | 12/1992 |

(Continued)

OTHER PUBLICATIONS

International Search Report and Written Opinion for PCT/US2009/051265.

(Continued)

*Primary Examiner* — Benjamin Sandvik

*Assistant Examiner* — Whitney T Moore

(74) *Attorney, Agent, or Firm* — Venable LLP; Henry J. Daley; Michael E. Nelson

(57) ABSTRACT n-type organic semiconductors have a pyromellitic diimide structure and electronic or electro-optic devices include pyromellitic diimide compounds as organic semiconductors. Specific semiconductors include pyromellitic diimide compounds have sidechains comprising fluorine substituted aliphatic or aromatic moieties linked to the pyromellitic diimide structure by an alkylene or heteroalkylene linking group. An electronic or electro-optic device includes a first electrode, a second electrode space apart from the first electrode, and an organic semiconductor layer arranged between the first and second electrodes. The organic semiconductor layer comprises a pyromellitic diimide compound.

26 Claims, 10 Drawing Sheets

Structure of Electronic Device

FOREIGN PATENT DOCUMENTS

| | | | |
|---|---|---|---|
| KR | 10-0559056 | B1 | 3/2006 |
| WO | WO-2008/085942 | A2 | 7/2008 |

OTHER PUBLICATIONS

Anthony, J. E. "Functionalzed acenes and heteroacenes for organic electronics", Chem. Rev., vol. 106, pp. 5028-5048, 2006.

Bendikov et al., "Tetrathiafulvalenes, oligoacenenes, and their buckminsterfullerene derivatives: the brick and mortar of organic electronics", Chem. Rev., vol. 104, pp. 4891-4945, 2004.

Carroll et al., "Redox modulation of benzene triimides and diimides via noncovalent interactions", Org. Lett, vol. 5, pp. 3177-3180, 2003.

Chen et al., "Air stable n-channel organic semiconductors for thin film transistors based on fluorinated derivatives of perylene diimides", Chem, Mater., vol. 19, pp. 816-824, 2007.

Crone et al., "Large-scale complementary integrated circuits based on organic transistors", Nature, vol. 403, pp. 521-523, 2000.

Gao et al., "Dibenzotetrathiafulvalene bisimides: new building blocks for organic electronic materials", Adv. Mater, vol. 19, pp. 3037-3042, 2007.

Hizu et al., "Reduction in orperation voltage of complementary organic thin-film transistor inverter circuits using double-gate structures", Applied Physics Letter, vol. 90, pp. 093504-1-093504-3, 2007.

Huang et al., "Hydroxy-terminated organic semiconductor-based field-effect transistors for phosphonate vapor detection", J. Am. Chem. Soc., vol. 129, 9366-9376, 2007.

Jones et al., "High-mobility air-stable n-type semiconductors with processing versatility: dicyanoperylene-3,4:9,10-bis(dicarboximides)", Angew. Chem. Int. Ed., vol. 43, pp. 6363-6366, 2004.

Jones et al., "Cyanonaphthalene diimide semiconductors for air-stable, flexible, and optically transparent n-channel field-effect Transistors", Chemistry of Materials, vol. 19, No. 11, pp. 2703-2705, 2007.

Jones et al., "Tuning orbital energentics in arylene diimide semiconductors. Materials design for ambient stability of n-type charge transport", J. Am. Chem. Soc., vol. 129, pp. 15259-15278, 2007.

Katz et al., "Synthetic chemistry for ultrapure, processable, and high-mobility organic transistor semiconductors", Acc. Chem. Res., vol. 34, pp. 259-369, 2001.

Katz et al., "A soluble and air-stable organic semiconductor with high electron mobility", Nature, vol. 404, pp. 478-481, 2000.

Kelley et al., "Recent progress in organic electronics: materials, devices, and processes," Chem. of Mater., vol. 16, pp. 4413, 2004.

Laquindanum et al., *J. Am. Chem. Soc*., vol. 118, pp. 11331, 1996.

Mori "Molecular materials for organic field-effect transistors", J. Phys.: Condens Matter, vol. 20, No. 184010, pp. 1-13, 2008.

Oh et al., "Air-stable n-channel organic thin-film transistors with high field-effect mobility based on N, N'-bis(heptafluorobutyl)-3,4:9,10-perylene diimide", Appl. Phys. Lett., vol. 91, pp. 212107-1-212107-3, 2007.

Parashkov et al., "Large area electronics using printing methods," Proceedings of the IEEE, vol. 93, No. 7, pp. 1321-1329, 2005.

Richardson "Thermochemical interpretation of electrode potentials for transition-metal complexes", Inorg. chem., vol. 29, pp. 3213-3217, 1990.

Schmidt et al., "Core-fluorinated perylene bisimide dyes: air stable n-channel organic semiconductors for thin film transistors with exceptionally high on-to-off current ratios", Adv. Mater., vol. 19, pp. 3692-3695, 2007.

Scudiero et al., "Scanning tunneling microscopy, orbital-mediated tunneling spectroscopy, and Itraviolet photoelectron spectroscopy of metal(II) tetraphenylporphyrins deposited from vapor", J. Am. Chem. Soc., vol. 123, pp. 4073-4080, 2001.

See et al., "Easily synthesized naphthalene tetracarboxylic diimide semiconductors with high electron mobility in air", Chem. Mater., vol. 20, pp. 3609-3616, 2008.

Sekitani et al., "A large-area wireless power transmission sheet using printed organic transistors and plastic MEMs switches," Nature Materials, vol. 6, pp. 413-417, 2007.

Someya et al, "Conformable, flexible, large-area networks of pressure and thermal sensors with organic transistor active matrixes," Proceedings of the National Academy of Sciences (USA), vol. 102, pp. 12321, 2005.

Steudel et al., "50MHz rectifier based on an organic diode," Nature Materials, vol. 4, pp. 597-600, 2005.

Steudel et al., "Comparison of organic diode structures regarding high-frequency rectification behavior in radio-frequency identification tags," Journal of Applied Physics, vol. 99, pp. 114519-1-114519-7, 2006.

Thompson et al., "Communications to the editor", Macromolecules, vol. 38, pp. 5359-5362, 2005.

Wang et al., "Anthracenedicarboximides as air-stable n-channel semiconductors for thin-film transistors with remarkable current on-off ratios", J. Am. Chem. Soc., vol. 129, pp. 13362-13363, 2007.

Weitz et al., "Organic n-channel transistors based on core-cyanated perylene caorboxylic diimide derivatives", J. Am. Chem. Soc., vol. 130, pp. 4637-4645, 2008.

Yang et al., "Ultrathin organic transistors for chemical sensing", Applied Physics Letters, vol. 90, pp. 263506-1-263506-3, 2007.

Kato et al., "Pyromellitic Diimide-Based Macrocycle with a Linear [pi]-Electronic System and Bis(phenylethynyl)pyromellitic Diimide: Syntheses, Structures, Photophysical Properties, and Redox Characteristics(1)",Journal of Organic Chemistry, vol. 73, No. 11, pp. 4063-4075, (2008).

Zheng et al., "Pyromellitic Diimides: Minimal Cores for High Mobility n-Channel Transistor Semiconductors", Journal of the Americal Chem. Society, vol. 130, No. 44, pp. 14410-14411, (2008).

* cited by examiner

Structure of Electronic Device

Crystal structure (left) and crystal packing diagram (right) of compound 1

Linear Absorption spectra for compounds 1 and 3 in $CH_2Cl_2$ ($9 \times 10^{-5}$M)

DSC thermogram of compound 1

DSC thermogram of compound 2

DSC thermogram of compound 3

X-ray diffraction pattern of 1 deposited at 25°C on an (a) untreated substrate, (b) OTS-SAM treated substrate, and (c) deposited at 65°C on an OTS-SAM treated substrate.

X-ray diffraction pattern of 1 deposited by solution process (2% DMF solution) on an OTS-SAM treated substrate.

X-ray diffraction pattern of 2 deposited at 115°C on an OTS-SAM treated substrate.

X-ray diffraction pattern of 3 deposited at 25°C on an OTS-SAM treated substrate.

AFM images of 1 deposited at 70°C on an OTS-SAM treated substrate.

AFM images of 1 deposited at 25°C on an (a) untreated substrate, (b) OTS-SAM treated substrate, and (c) deposited at 65°C on an OTS-SAM treated substrate.

CV Traces for compound 1.

CV Traces for compound 3.

Current-voltage characteristics of 4 prepared by solution process.

Current-voltage characteristics of 1 and 2 prepared by sublimation at a substrate temperature of $T_d$ = 70°C and 115°C respectively. a) a plot of $I_d$ versus $V_d$ for compound 1; b) a plot of $I_{d\text{-sat}}$ versus $V_g$ for compound 1; c) a plot of $I_d$ versus $V_d$ for compound 2; d) a plot of $I_{d\text{-sat}}$ versus $V_g$ for compound 2.

PYROMELLITIC DIIMIDE ORGANIC SEMICONDUCTORS AND DEVICES

CROSS-REFERENCE TO RELATED APPLICATION

This application claims priority to U.S. Provisional Application Nos. 61/082,284 and 61/082,339, both filed Jul. 21, 2008, the entire contents of which are hereby incorporated by reference, and is a U.S. national stage application under 35 U.S.C. §371 of PCT/US2009/051265 filed Jul. 21, 2009, the entire contents of which are incorporated herein by reference.

This invention was made using U.S. Government support under AFOSR Grant No. FA9550-06-01-0076. The U.S. Government has certain rights in this invention.

BACKGROUND

1. Field of Invention

The current invention relates to semiconductor compositions and devices that use the semiconductor compositions, and more particularly to pyromellitic diimide semiconductors and devices that include the pyromellitic diimide semiconductors.

2. Discussion of Related Art

The past decade has witnessed an increasing interest in organic thin film transistors (OTFTs) due to their applications in light-emitting displays, radio-frequency identification tags, and sensors, for example (Org. Electronics (Ed: H. Klauk), Wiley-VCH, Weinheim, Germany 2006; Bendikov, M.; Wudl, F.; Perepichka, D. F. *Chem. Rev.* 2004, 104, 4891; Anthony, J. E. *Chem. Rev.* 2006, 106, 5028; Katz, H. E.; Bao, Z.; Gilat, S. L. Acc. *Chem. Res.* 2001, 34, 359; Yang, R. D.; Gredig, T.; Colesniuc, C. N.; Park, J.; Schuller, I. K.; Trogler, W. C.; Kummel, A. C. *Appl. Phys. Lett.* 2007, 90, 263506; Huang, J.; Miragliotta, J.; Becknell, A.; Katz, H. E. *J. Am. Chem. Soc.* 2007, 129, 9366). Organic semiconductors can function either as a p-channel or n-channel charge carrier. While many organic materials can be used for p-channel OTFTs, there is only a limited number of available organic materials that can be used for n-channel OTFTs (Org. Electronics (Ed: H. Klauk), Wiley-VCH, Weinheim, Germany 2006; Bendikov, M.; Wudl, F.; Perepichka, D. F. *Chem. Rev.* 2004, 104, 4891; Anthony, J. E. *Chem. Rev.* 2006, 106, 5028; Katz, H. E.; Bao, Z.; Gilat, S. L. *Acc. Chem. Res.* 2001, 34, 359; Yang, R. D.; Gredig, T.; Colesniuc, C. N.; Park, J.; Schuller, I. K.; Trogler, W. C.; Kummel, A. C. *Appl. Phys. Lett.* 2007, 90, 263506; Mori, T. *J. Phys.: Condens. Matter* 2008, 20, 184010; Gao, X; Wang, Y; Yang, X; Liu, Y; Qiu, W; Wu, W; Zhang, H; Qi, T.; Liu, Y.; Lu, K; Du, C.; Shuai Z.; Yu, G. and Zhu, D. B. *Adv. Mater.* 2007, 19, 3037). Therefore, there is a need for more n-channel materials with high mobility and stability, for example to allow for combining n-channel and p-channel transistors in complementary circuits which have advantages of low power dissipation, low noise and greater operational stability (Crone, B.; Dodabalapur, A.; Lin, Y. Y.; Filas, R. W.; Bao, Z.; LaDuca, A.; Sarpeshkar, R.; Katz, H. E.; Li, W. *Nature* 2000, 403, 521; Hizu, K.; Sekitani, T.; Someya, T.; Otsuki, J. *Appl. Phys. Lett.* 2007, 90, 093504). Since the report of naphthalenetetracarboxylic diimides as air stable n-channel materials with mobility up to 0.1 $cm^2/(V.s)$, a large number of n-channel materials have been based on either naphthalene or perylene tetracarboxylic diimides (Laquindanum, J. G.; Katz, H. E.; Dodabalapur, A.; Lovinger, A. J. *J. Am. Chem. Soc.* 1996, 118, 11331; Katz, H. E.; Lovinger, A. J.; Johnson, J.; Kloc, C.; Siegrist, T.; Li, W.; Lin, Y. Y.; Dodabalapur, A. *Nature* 2000, 404, 478; Jones, B. A.; Ahrens, M. J.; Yoon, M.-H.; Facchetti, A.; Marks, T. J.; Wasielewski, M. R. *Angew. Chem. Int. Ed.* 2004, 43, 6363; Jones, B. A.; Facchetti, A.; Marks, T. J.; Wasielewski, M. R. *Chem. Mater.* 2007, 19, 2703; Jones, B. A.; Facchetti, A.; Wasielewski, M. R.; Marks, T. J. *J. Am. Chem. Soc.* 2007, 129, 15259; Chen, H. Z.; Ling, M. M.; Mo, X.; Shi, M. M.; Wang, M.; Bao, Z. *Chem. Mater.* 2007, 19, 816; Schmidt, R.; Ling, M. M.; Oh, J. H.; Winkler, M.; Konemann, M.; Bao, Z.; Wurthner, F. *Adv. Mater.* 2007, 19, 3692; Weitz, R. T.; Amsharov, K.; Zschieschang, U.; Villas, E. B.; Goswami, D. K.; Burghard, M.; Dosch, H.; Jansen, M.; Kern, K.; Klauk, H. *J. Am. Chem. Soc.* 2008, 130, 4637; See, K. C.; Landis, C.; Sarjeant, A.; Katz, H. E. *Chem. Mater.* 2008, 20, 3609; Oh, J. H.; Liu, S.; Bao, Z.; Schmidt, R.; Wurthner, F. *Appl. Phys. Lett.* 2007, 91, 212107-3). Recently, several anthracene tetracarboxylic diimides were synthesized by Marks et al through multi-step reactions and found to be good n-channel materials with high on-off ratios (Wang, Z.; Kim, C.; Facchetti, A.; Marks, T. J. *J. Am. Chem. Soc.* 2007, 129, 13362). The common structural features, the tetracarboxylic diimides, were flanked on both sides of the planar aromatic rings, which were varied from two-ring naphthalene to three-ring anthracene, and finally to five-ring perylene.

Though pyromellitic dimides are best known as segments of highly insulating polyimide dielectrics, it is nevertheless appears that no attempt has been made to fabricate transistors from pyromellitic diimide derivatives, which have the simplest aromatic ring (benzene) in the center, and the tetracarboxylic diimides on both sides of the benzene ring. Pyromellitic diimide derivatives can be easily prepared by one-step reaction between pyromellitic dianhydride and various amines. Thus, there remains a need for improved organic semiconductors and devices that use the improved organic semiconductors

SUMMARY

The present invention relates to n-type organic semiconductors having a pyromellitic diimide structure. In certain embodiments, the n-type organic semiconductors have the structure of Formula I, shown below.

Formula I

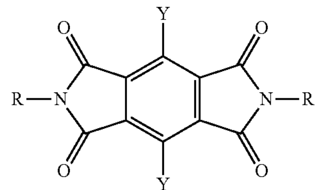

wherein Y is selected from the group consisting of hydrogen, A, or one of the structures shown below:

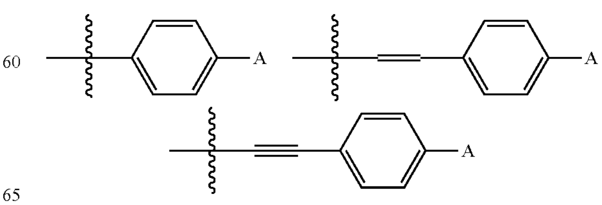

wherein A is an electron withdrawing substituent. R is one of structures II, III, IV, V or VI

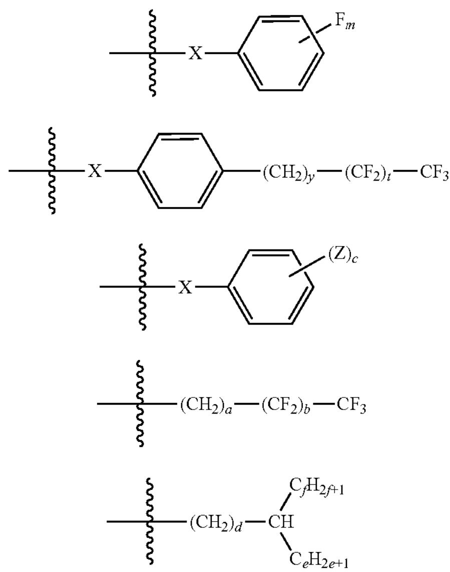

wherein X is —$(CH_2)_v$—, —$(CH_2)_w$—O—, or —$(CH_2)_w$—O—$(CH_2)_v$—; Z is —$OC_nF_{(2n+1)}$, or —$C_nF_{(2n+1)}$ where n is 1, 2 ,3 or 4; a is independently 1, 2, 3, or 4; b is an integer from 1 to 20; c is 1, 2 or 3; d is independently 0, 1, 2, 3, or 4; e and f are independently integers from 2 to 12; v is independently 1, 2, 3, or 4, and w is independently 2, 3, or 4; m is an integer from 1 to 5; y is each independently 0, 1, 2, 3, or 4; and t is an integer from 1 to 20.

Some embodiments of the present invention also include electronic or electro-optic devices using pyromellitic diimide compounds as organic semiconductors. In some embodiments, the devices include compounds having Formula I.

An electronic or electro-optic device according to an embodiment of the current invention includes a first electrode, a second electrode space apart from the first electrode, and an organic semiconductor layer arranged between the first and second electrodes. The organic semiconductor layer comprises a pyromellitic diimide compound.

DETAILED DESCRIPTION OF VARIOUS EMBODIMENTS

Figure 1:
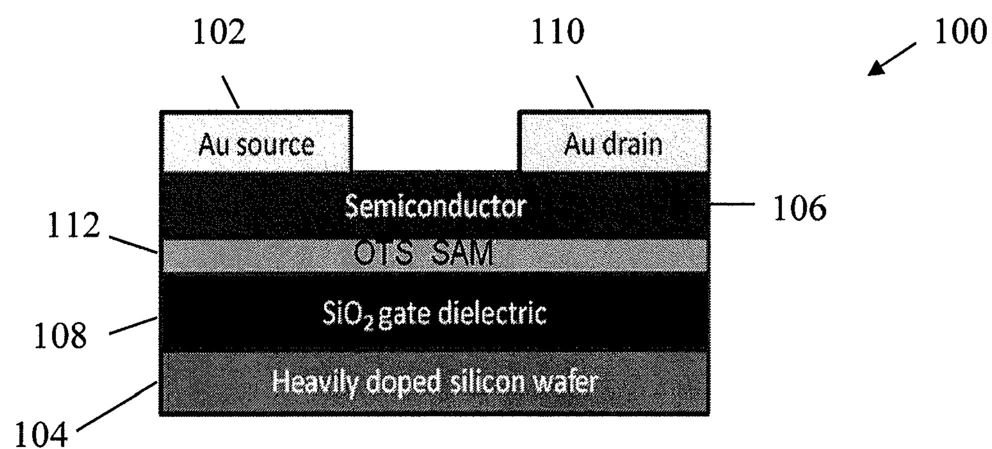
FIG. 1 is a schematic illustration of an electronic or electro-optic device according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited herein are incorporated by reference as if each had been individually incorporated.

Embodiments of the present invention include novel n-type organic semiconductors having a pyromellitic diimide (PyDI) structure of Formula I:

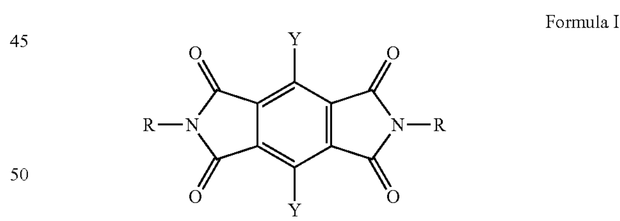

wherein Y is selected from the group consisting of hydrogen, A, or one of the structures shown below:

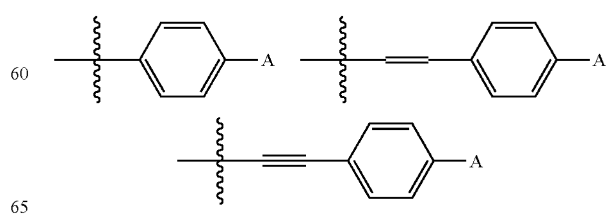

wherein A is an electron withdrawing substituent. R is one of structures II, III, IV, V or VI

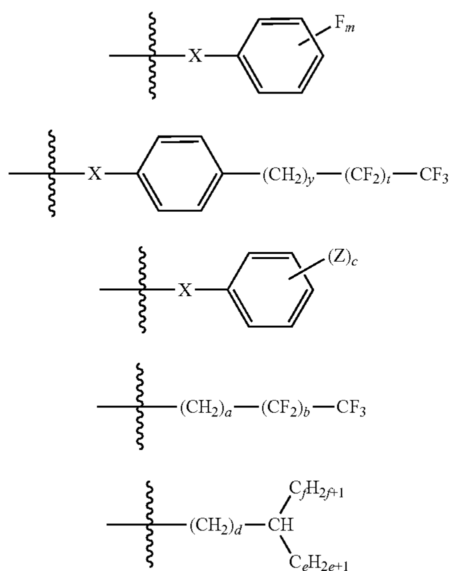

wherein X is —$(CH_2)_v$—, —$(CH_2)_w$—O—, or —$(CH_2)_w$—O—$(CH_2)_v$—; Z is —$OC_nF_{(2n+1)}$, or —$C_nF_{(2n+1)}$ where n is 1, 2 ,3 or 4; a is independently 1, 2, 3, or 4; b is an integer from 1 to 20; c is 1, 2 or 3; d is independently 0, 1, 2, 3, or 4; e and f are independently integers from 2 to 12; v is independently 1, 2, 3, or 4, and w is independently 2, 3, or 4; m is an integer from 1 to 5; y is each independently 0, 1, 2, 3, or 4; and t is an integer from 1 to 20.

The phrase "an integer from" specifically includes all integers between the upper and lower limit. For example, "m is an integer from 1 to 5" means that m may be 1, 2, 3, 4, or 5.

In certain embodiments Y is hydrogen atom. In other embodiments Y is not hydrogen, and may be A or one of the structures shown below.

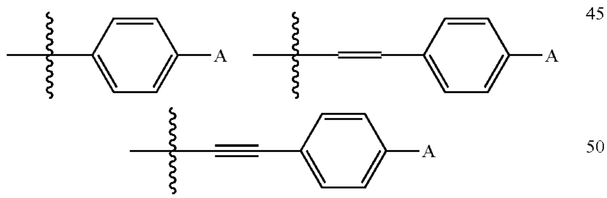

wherein A is an electron withdrawing substituent. An electron withdrawing substituent is an electron withdrawing group as generally understood in the art of organic chemistry, as a substituent which decreases the electron density of the π system. Examples of electron withdrawing groups include halogens, including fluorine, chlorine, bromine and iodine; cyano; nitro; fluorinated alkyls having the formula $C_nF_{(2n+1)}$ where n is 1, 2, 3, or 4; fluorinated alkoxy groups having the formula —$OC_nF_{(2n+1)}$ where n is 1, 2, 3, or 4; and fluorinated carbonyl groups having the formula —$C(O)C_nF_{(2n+1)}$. The group $C_nF_{(2n+1)}$ includes linear or branched groups and may be, for example, trifluoromethyl ($CF_3$), pentafluoroethyl ($C_2F_5$), perfluoropropyl ($CF_2CF_2CF_3$), perfluoroisopropyl ($CF(CF_3)_2$, perfluorobutyl ($CF_2)_3CF_3$) or perfluoroisobutyl ($CF_2CF(CF_3)$). Electron-withdrawing groups can also include ethenyl or ethynyl groups substituted with one or more other electron withdrawing groups, such as cyano, perfluoroalkyl, or nitro. For cases where Y is one of the structures containing an aromatic ring, A may be a carbonyl functionality, such as a ketone or an ester.

Examples of some embodiments include the compounds shown below.

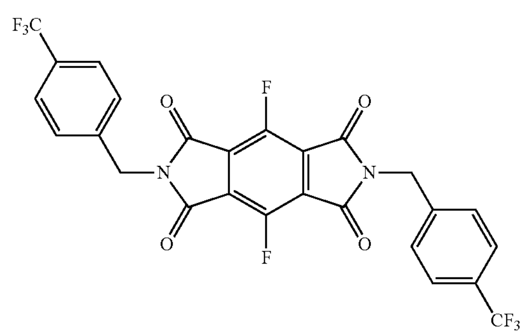

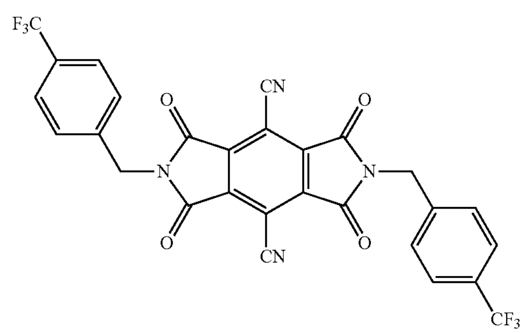

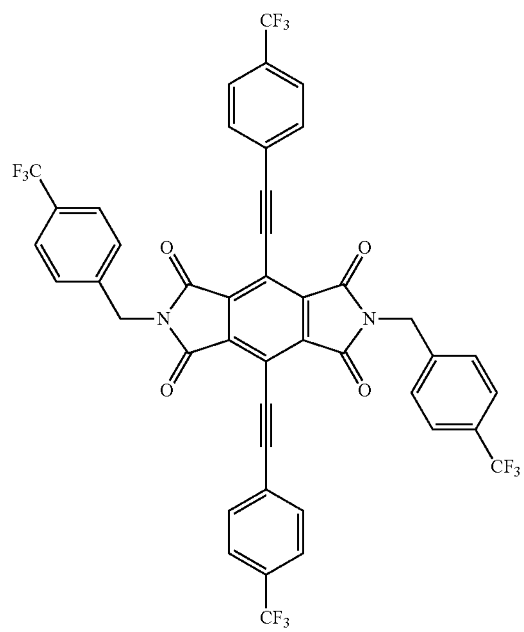

In some embodiments, R is structure II shown below:

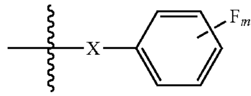

wherein X is —$(CH_2)_v$—, —$(CH_2)_w$—O—, or —$(CH_2)_w$—O—$(CH_2)_v$—; and m is 1, 2, 3, 4, or 5. In these embodiments, the phenyl ring may have one or more fluorine substituents. In cases where there are less than 5 fluorine substituents, the substituents may be at any position on the phenyl ring.

In certain embodiments, R has the structure

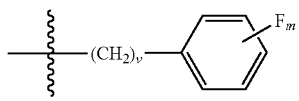

wherein v is 1 or 2, and m is 1, 2, 3, 4 or 5. In certain specific embodiments, v is 2 and m is 5. In other embodiments, v is 2 and m is 1, and the fluorine is located at the para position.

Examples of some embodiments include the compounds shown below:

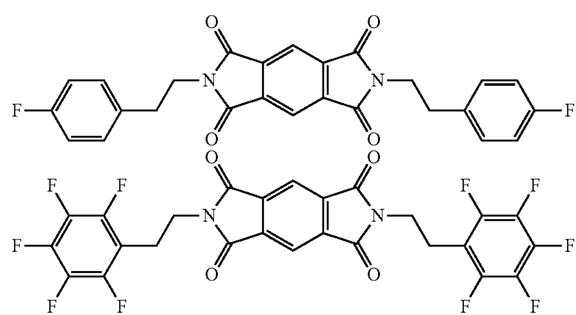

In some embodiments, R is structure III shown below:

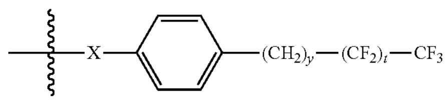

wherein X is —$(CH_2)_v$—, —$(CH_2)_w$—O—, or —$(CH_2)_w$—O—$(CH_2)_v$—; y is each independently 0, 1, 2, 3, or 4; and t is an integer from 1 to 20. In these embodiments, the sidechain may have any number of —$CF_2$— units from 1 to 20 inclusively. Accordingly, t may also be an integer from 2-12, 3-10, or 5-9.

In certain embodiments, R has the structure

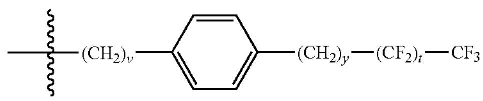

wherein v is 1 or 2, y is 1 or 2, and t is 5, 6, 7, 8 or 9. In certain exemplary embodiments, v is 1, y is 2 and t is 7, as shown in the structure below.

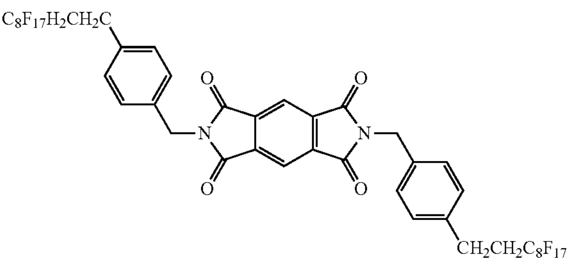

In some embodiments, R is structure IV shown below:

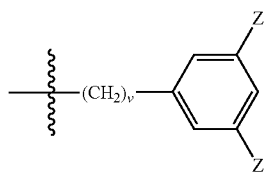

wherein X is —$(CH_2)_v$—, —$(CH_2)_w$—O—, or —$(CH_2)_w$—O—$(CH_2)_v$—; Z is —$OC_nF_{(2n+1)}$, or —$C_nF_{(2n+1)}$ where n is 1, 2 ,3 or 4; and c is 1, 2, or 3 . In these embodiments, the phenyl ring may have one or more than one substituent Z. Z may be a fluorinated alkoxy substituent of the formula —$OC_nF_{(2n+1)}$ or a fluorinated alkyl substituent of the formula —$C_nF_{(2n+1)}$. As discussed previously, the group $C_nF_{(2n+1)}$ includes linear or branched groups and may be, for example, trifluoromethyl ($CF_3$), pentafluoroethyl ($C_2F_5$), perfluoropropyl ($CF_2CF_2CF_3$), perfluoroisopropyl ($CF(CF_3)_2$, perfluorobutyl ($(CF_2)_3CF_3$) or perfluoroisobutyl ($CF_2CF(CF_3)$).

In certain specific embodiments, R has the structure wherein v is 1 or 2. In this case, Z may be —$OC_nF_{(2n+1)}$, or —$C_nF_{(2n+1)}$ where n is 1, 2, 3 or 4. In certain embodiments, Z is trifluoromethyl.

Examples of some embodiments include the compound shown below.

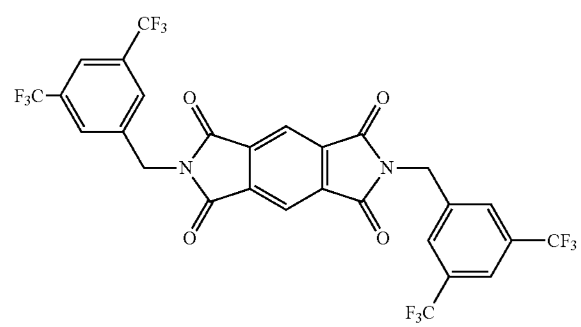

In other specific embodiments, R has the structure

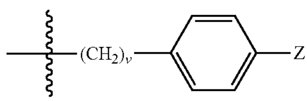

wherein v is 1 or 2. Again, Z may be —$OC_nF_{(2n+1)}$, or —$C_nF_{(2n+1)}$ where n is 1, 2, 3 or 4. In certain embodiments, Z is trifluoromethyl.

Examples of some embodiments include the compounds shown below.

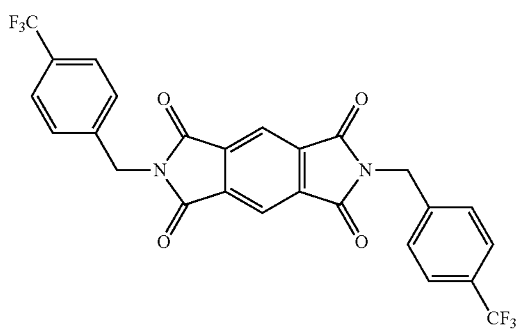

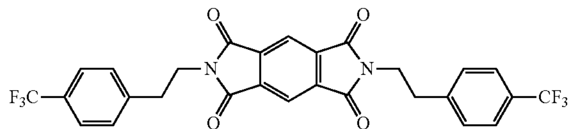

In some embodiments, R is structure V shown below:

V

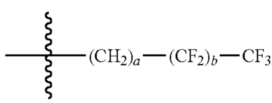

wherein a is 1, 2, 3, or 4 and b is an integer from 1 to 20. In these embodiments, R is a fluorinated alkyl chain of varying lengths. As discussed previously the sidechain may have any number of —$CF_2$— units from 1 to 20. In certain embodiments a is 1 or 2, and b is 5, 6, 7, 8, or 9. In some embodiments, a is 1 and b is 3 as shown below.

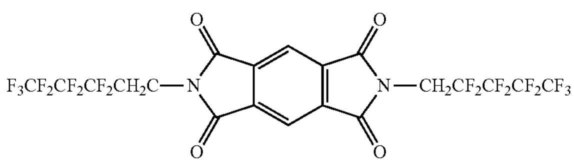

In some embodiments, R is structure VI shown below:

VI

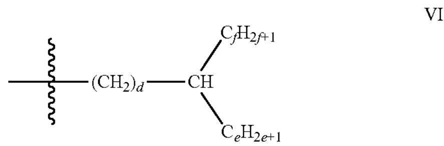

wherein d is independently 0, 1, 2, 3, or 4; e and f are independently integers from 2 to 12. In these embodiments, R is a branched alkyl chain having at least one branch point. The branches are independent, meaning e and f may be the same or different lengths. The separate branches may include further branch points or may be linear. A linear segment may or may not be present between the branch point and the pyromellitic diimide core (i.e. d may be 0). In certain embodiments, d is 1, e is 2, and f is 4. In other embodiments, d is 0, and e and f are both 6. In other embodiments, d is 1, e is 10, and f is 12.

The compounds of the present invention can be conveniently prepared by procedures known in the art. For example, 3,6-unsubstituted compounds may be prepared by reaction of the appropriate primary amine with pyromellitic dianhydride. Substituted compounds may be prepared from a substituted pyromellitic dianhydride precursor, such as 3,6-dibromopyromellitic dianhydride, as outlined in the scheme below. The bromide substituents may be displaced by other nucleophiles. Examples of displacement with fluoride and CN are shown in the scheme below. The dibromo compounds may also be modified by metal-catalyzed cross-coupling reactions with aromatic, alkenyl, or alkynyl reagents. An illustration of a reaction between a dibromopyromellitic compound and an alkynyl reagent is shown in the scheme below.

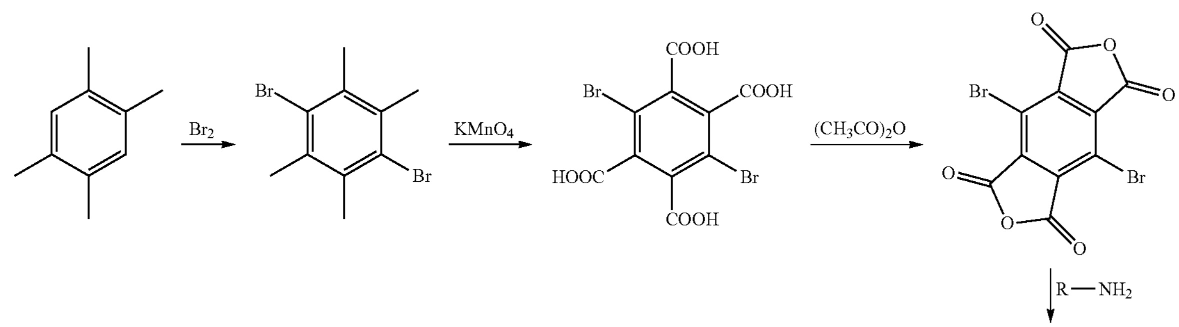

-continued

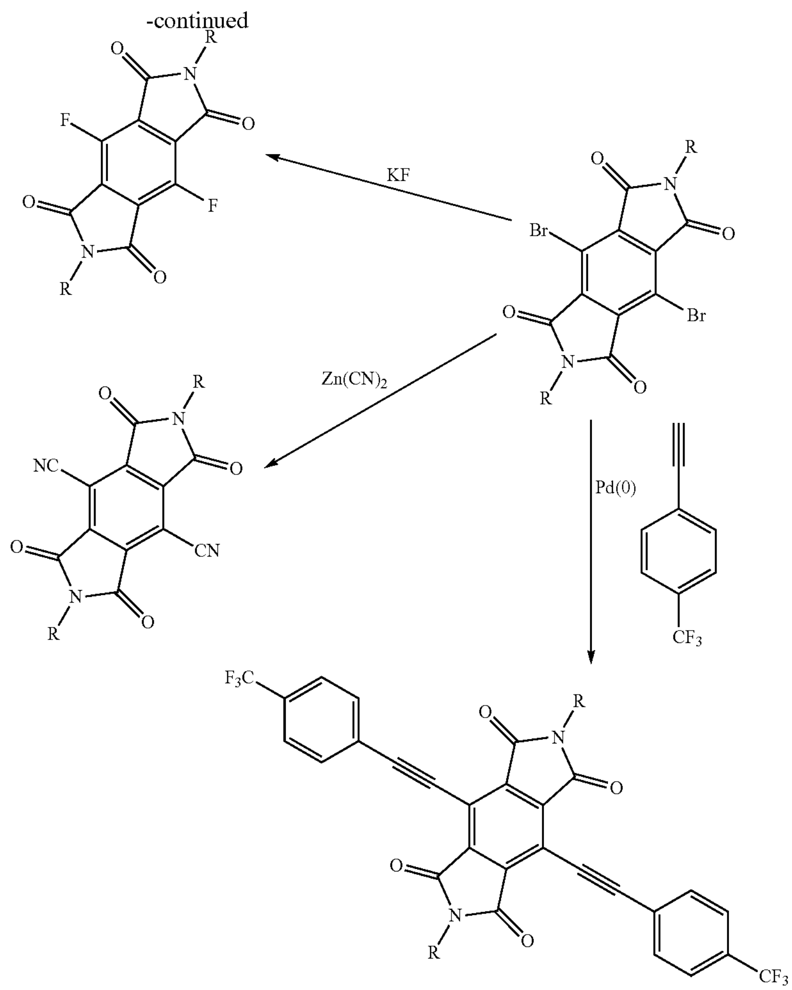

It is understood that these syntheses are illustrative, and that modifications or other syntheses may be used by those skilled in the art to prepare the compounds of this invention.

The compounds of the present invention form semiconductor films, deposited onto a substrate by any suitable method. For example, vapor phase deposition, including rapid sublimation may be used to deposit the compound onto a suitable substrate. Likewise, solvent processing, including dip coating, drop casting, spin coating or blade coating may be used. The semiconducting layer may include one or more layers of the semiconducting material.

Thin films comprising the compounds of the present invention have high electron mobilities. Films of the compounds may have electron mobilities greater than about 0.01 $cm^2/Vs$. Mobilities are calculated from the saturation regime and fitted in the regions of highest slope. Thin films comprising the compounds of the invention may also have high electron mobilities in air. In which case, the electron mobility in air is greater than about 0.01 $cm^2/Vs$.

Devices according to some embodiments of the current invention include one or more of the above-described compounds.

An electronic or electro-optic device 100 according to an embodiment of the current invention is illustrated schematically in FIG. 1. The electronic or electro-optic device 100 has a first electrode 102, a second electrode space 104 apart from said first electrode 102, and an organic semiconductor layer 106 arranged between the first and second electrodes (102, 104). The organic semiconductor layer 106 comprises a pyromellitic diimide compound. The pyromellitic diimide compound can be selected from the above-described n-channel pyromellitic diimide compounds according to some embodiments of the current invention. The organic semiconductor layer 106 has a maximum charge mobility of at least about 0.01 $cm^2/Vs$ in air according to some embodiments of the current invention, or at least about 0.02 $cm^2/Vs$ in air according to some embodiments of the current invention, or at least about 0.05 $cm^2/Vs$ in air according to some embodiments of the current invention.

The electronic or electro-optic device 100 further includes a dielectric layer 108 formed on the second electrode 104 between the semiconductor layer 106 and the second electrode 104, and a third electrode 110 spaced apart from the first electrode 102 and the second electrode 104. In the example of FIG. 1, the first electrode 102 is a source electrode, the second electrode 104 is a gate electrode and the third electrode 110 is a drain electrode such that the electronic or electro-optic device 100 is a field effect transistor. However, the invention is not limited to only field effect transistors. Other embodiments can include one or more of any of known device that can be made with semiconductors. For example, devices according to the current invention can include one or more two-electrode, three-electrode, four-electrode or more electronic or electro-optic devices. Furthermore, transistors according to the current invention are not limited to only field effect transistors. Devices according to various embodiments of the current invention can be, without limitation, diodes, transistors, photovoltaic cells, photodiodes, and light-emitting diodes, for example. Devices according to some embodiments of the current invention can include two or more semiconductor layers and can include one or more additional layers of material to provide desired effects according to the particular application.

In the electronic or electro-optic device 100, the first and third electrodes (102, 110) are gold, the second electrode is heavily doped silicon wafer and the dielectric layer 108 is silicon dioxide. However, devices 100 are not limited to only these materials. The electronic or electro-optic device 100 can also include a self assembled monolayer 112 formed on the dielectric layer 108 to enhance the electron mobility of the semiconductor layer according to some embodiments of the current invention. The electronic or electro-optic device 100 can have an on-off ratio of at least about $10^3$ in air according to some embodiments of the current invention.

Additionally, transistors comprising thin films using the compounds of the present invention can have high on/off ratios according to some embodiments of the current invention. These devices may have on/off ratios of at least about $10^4$ in some embodiments, at least about $10^5$ in some embodiments and at least about $10^6$ in some embodiments. The high on/off ratios may also be present when operated in air. In such cases, the on/off ratio in air may be at least about $10^3$ in some embodiments, at least about $10^4$ in some embodiments and at least about $10^5$ in some embodiments.

Applications of these new materials may include high-speed plastic-based circuits taking advantage of shorter channels available because of high-capacitance gates, flexible and pressure-sensitive circuits, supercapacitors, and solar cells where the side chains may promote preferred bulk heterojunction morphology. In some embodiments, films of pyromellitic diimide compounds of the present invention can be used in thin film transistors, and complementary inverter circuits, for example. The devices can be transparent and/or translucent according to some embodiments of the current invention.

Such TFTs and other devices are useful in electronic devices, including for example, more complex circuits, such as shift registers, integrated circuits, or logic circuits, active matrix displays, and ring oscillators, for example. In certain embodiments, organic/printed active electronics may provide control, amplification, and logic. For example, applications may be in circuits of moderate complexity, such as display drivers, radio frequency identification tags, or pressure mapping elements. (T. W. Kelley, P. F. Baude, C. Gerlach, D. E. Ender, D. Muyres, M. A. Haase, D. E. Vogel, and S. D. Theiss, "Recent progress in organic electronics: Materials, devices, and processes," Chemistry Of Materials 16, 4413 (2004); T. Someya, Y. Kato, T. Sekitani, S. Iba, Y. Noguchi, Y. Murase, H. Kawaguchi, and T. Sakurai, "Conformable, flexible, large-area networks of pressure and thermal sensors with organic transistor active matrixes," Proceedings Of The National Academy Of Sciences Of The United States Of America 102, 12321 (2005); R. Parashkov, E. Becker, T. Riedel, H.-H. Johannes, and W. Kowalsky, "Large area electronics using printing methods," Proceedings Of The Ieee 93, 1321 (2005). Additional embodiments can include complex organic-based circuitry for radiofrequency identification tags, where MHz switching speeds have been demonstrated. (S. Steudel, S. De Vusser, K. Myny, M. Lenes, J. Genoe, and P. Heremans, "Comparison of organic diode structures regarding high-frequency rectification behavior in radio-frequency identification tags," Journal Of Applied Physics 99 (2006); S. Steudel, K. Myny, V. Arkhipov, C. Deibel, S. De Vusser, J. Genoe, and P. Heremans, "50 MHz rectifier based on an organic diode," Nature Materials 4, 597 (2005).) Exemplary embodiments may further include wireless power distribution. (T. Sekitani, M. Takamiya, Y. Noguchi, S. Nakano, Y. Kato, T. Sakurai, and T. Someya," A large-area wireless power transmission sheet using printed organic transistors and plastic MEMs switches," Nature Materials 6, 413 (2007).)

A support, may be used for supporting the device during manufacturing, testing, and/or use. The support can be, but is not limited to, a substrate. The skilled artisan will appreciate that a support selected for commercial embodiments may be different from one selected for testing or screening various embodiments. In some embodiments, the support does not provide any necessary electrical function. This type of support is termed a "non-participating" support. Useful materials can include organic or inorganic materials. For example, the support may comprise inorganic glasses, ceramic foils, polymeric materials, filled polymeric materials, coated metallic foils, acrylics, epoxies, polyamides, polycarbonates, polymimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylenesulfide) (PPS), and fiber-reinforced plastics.

In certain embodiments, a flexible support is used. This allows for roll processing, which may be continuous, providing economy of scale and economy of manufacturing over flat and/or rigid supports, and enables the production of flexible electronic devices. Flexible supports however, require a low substrate temperature for deposition.

In certain embodiments, the films are formed with a substrate temperature at room temperature. In other embodiments, the films are deposited at a higher substrate temperature. For example, the films may be deposited at a substrate temperature of 40, 60, 65, 70, 80, 100, 110, 115° C. or higher. At these substrate temperatures, the electron mobility of the deposited films is greater than 0.01 $cm^2/Vs$.

In some embodiments, the support is optional. For example, but not limited to, when the gate electrode provides sufficient support for the intended use of the resultant OTFT, the support is not required. In addition, the support may be combined with a temporary support. In such an embodiment, one support may be detachably adhered or mechanically affixed to another support such as when one support is desired for a temporary purpose, e.g. manufacturing, transport, testing, and/or storage. For example, a flexible polymeric support may be adhered to a rigid glass support, which could be removed.

The gate electrode can be any useful conductive material. A variety of gate materials known in the art are also suitable, including metals, degenerately doped semiconductors, conducting polymers, and printable materials such as carbon ink or silver-epoxy. For example, the gate electrode may comprise doped silicon, or a metal, such as aluminum, chromium, gold, silver, nickel, palladium, platinum, tantalum and titanium. Conductive polymers can also be used, for example polyaniline, poly(3,4-ethylenedioxythiophene/poly(styrene sulfonate) (PEDOT:PSS). In addition, alloys, combinations and multilayers of these materials may be useful.

In certain embodiments the organic semiconducting compounds may be used in conjunction with a dielectric layer. In some embodiments the gate dielectric may be formed by oxidizing the gate electrode material to form the gate dielectric, or may be formed by deposition of a separate dielectric layer. The dielectric layer may be formed of any suitable material. The dielectric constant of the dielectric layer can vary widely depending on the particular device and circumstance of use. Useful materials for the gate dielectric may comprise, for example, an inorganic electrically insulating material, such as strontiates, tantalates, titanates, zirconates, aluminum oxides, silicon oxides, silicon nitrides, barium titanate, barium strontium titanate, barium zirconate titanate, zinc selenide, or zinc sulfide. The gate dielectric may comprise a polymeric material, such as polyvinylidenedifluoride (PVDF), cyanocelluloses, polyimides, etc. Alloys, combinations, mixtures and multilayers may also be used for the dielectric layer.

In certain embodiments, a separate dielectric layer can be a material that has electrically non-conducting planar structures with intercalated ions therebetween. The intercalated ions can be free to move in two dimensions between the electrically non-conducting planes, while being impeded from moving to the electrodes by the electrically non-conducting planes. In operation, the ions of the separate dielectric material can be polarized by an applied voltage. The dielectric layer may be, for example, sodium beta-alumina (Na-$\beta Al_2O_3$) or sodium beta-double-prime alumina in some embodiments. However, the dielectric layer is not limited to only these particular examples.

In some embodiments, a self-assembled monolayer (SAM) may be used to treat the electrode or dielectric surface prior to deposition of the organic semiconductor. In exemplary embodiments, the SAM may be formed by treatment of the electrode or dielectric surface with a solution of a silane compound to form a silane monolayer. The self-assembled monolayer may be formed, for example, by octadecyltrimethoxysilane or perfluorodecyltrimethoxysilane.

The source electrode and drain electrode are separated from the gate electrode by the pyromellitic diimide semiconductor material. In other embodiments, there can be additional dielectric layers and/or additional layers of other materials between the drain and source electrodes. In some embodiments, there can be multiple layers of semiconductor materials between the source and drain electrodes and the gate electrode. For example, there can be a p-channel semiconductor layer in addition to an n-OSC layer to provide devices with a p-n junction according to some embodiments of the current invention. The n-channel and p-channel semiconducting layers can be arranged with one on top of the other or side-by-side in some embodiments of the current invention. The source and drain electrodes can be any useful conductive material, including most of those materials described above for the gate electrode, for example, aluminum, barium, calcium, chromium, gold, silver, nickel, palladium, platinum, titanium, polyaniline, PEDOT:PSS, other conducting polymers, alloys thereof and multilayers thereof.

The thin film electrodes (e.g. gate electrode, source, electrode, and drain electrode) can be provided by any useful means such as physical vapor deposition (e.g. thermal evaporation or sputtering) or ink jet printing. The patterning of those electrodes can be accomplished by known methods such as shadow masking, additive photolithography, subtractive photolithography, printing, microcontact printing, and pattern coating.

The examples disclosed below are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

EXAMPLES

A. Synthesis Procedure

General $^1H$ NMR spectra were recorded on Bruker Avance (300 MHz/400 MHz) spectrometers. Mass spectra (MALDI-TOF) were acquired on a Bruker Autoflex device using 2,5-dihydroxybenzoic acid (DHB) as the matrix at the University of Kentucky Mass Spectrometry Facility. Linear absorption spectra were measured at room temperature using a Varian Cary 50 Bio UV-Vis spectrophotometer. DSC measurements were carried out by using a TA DSC Q20 modulated instrument at a heating rate of 10° C./min under a nitrogen atmosphere. The electrochemical measurements were carried out in dichloromethane solutions under $N_2$ with 0.1 M tetrabutylammonium hexafluorophosphate ($NBu_4PF_6$) as the supporting electrolyte at room temperature. A platinum disk and platinum wire were used as a working and counter electrode, respectively. The cyclic voltammograms were obtained at a scan rate of 200 mV/sec. We used Ag/AgCl in saturated NaCl aqueous solution as a reference electrode (Thompson, B. C.; Kim, Y-G.; and Reynolds, J. R. *Macromolecules,* 2005, 38, 5359; Bard, A. J.; Faulkner, L. R. *Electrochemical Methods: Fundamentals and Applications,* 2nd ed.; Wiley: New York, 2001; Scudiero, L.; Barlow, Dan E.; Mazur, U.; Hipps, K. W. *J. Am. Chem. Soc.* 2001, 123, 4073; Richardson, D. E. *Inorg. Chem.* 1990, 29, 3213). Elemental analysis was carried by Atlantic Analysis Inc., Norcross, Ga. 4-(1H,1H,2H,2H-Perfluorodecyl) benzylamine was purchased from Fluorous Technologies Inc. 1H,1H,-Perfluoropentylamine was supplied by Matrix Scientific. Pyromellitic dianhydride, 4-(trifluoromethyl)benzylamine are commercially available from Aldrich. Density function theory (DFT) calculations were performed with Gaussian 03 program package (Gaussian Inc.).

Example compounds were prepared according to the following scheme

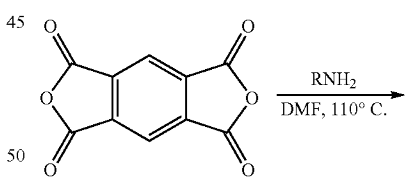

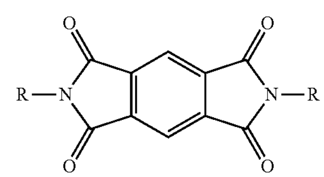

-continued

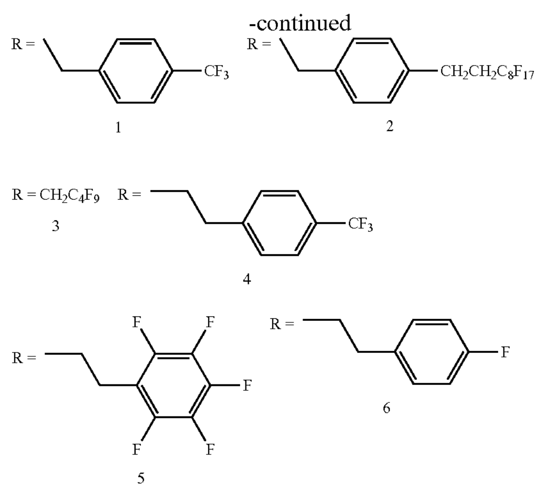

Example 1

N,N'-Di(4-(trifluoromethyl)benzyl)pyromellitic diimide (1)

4-(Trifluoromethyl)benzylamine (0.91 g, 5.2 mmol) and pyromellitic dianhydride (0.55 g, 2.5 mmol) were dissolved in DMF (20 mL), then the mixture was stirred at 110° C. overnight. After cooling to ambient temperature, the mixture was filtered and washed with methanol and a white solid (1.20 g, 90%) was obtained. The crude product was purified by vacuum sublimation. Elemental analysis: calcd for C, 58.66; H, 2.65; F, 21.41; N, 5.26; found: C, 58.73; H, 2.57, F, 21.69; N, 5.27. Mp 263-264° C. MALDI-TOF/MS, m/z calcd for $C_{26}H_{14}F_6N_2O_4$: 532, found: 532; $^1$H NMR (300 MHz, $CDCl_3$, ppm): δ=4.97 (s, 4H), 7.63 (d, J=8.4 Hz, 4H), 7.75 (d, J=8.4 Hz, 4H), 8.31 (s, 2H).

Figure 2:
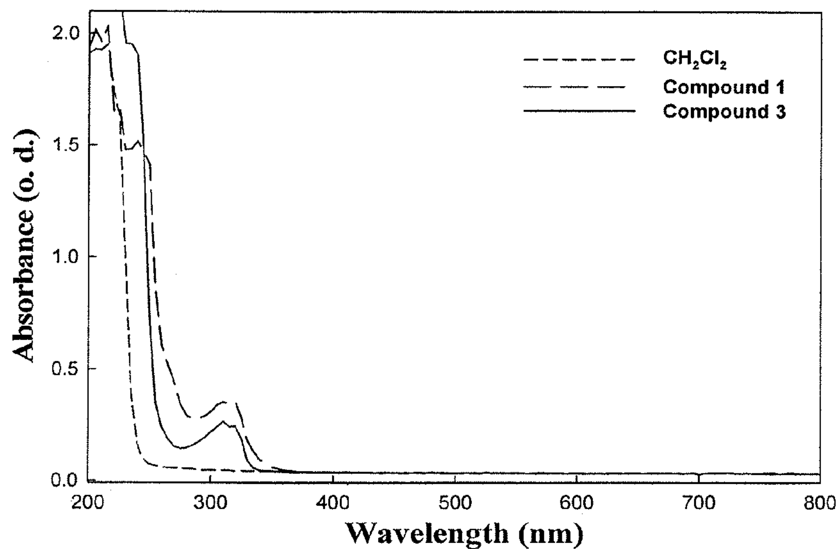
FIG. 2 shows Linear Absorption spectra for compounds 1 and 3 in $CH_2Cl_2$ ($9\times10^{-5}$M).

A Linear Absorption spectrum for compound 1 in $CH_2Cl_2$ ($9\times10^{-5}$M) is shown in FIG. 2 showing low absorption across the entire visible wavelength range.

Figure 3:
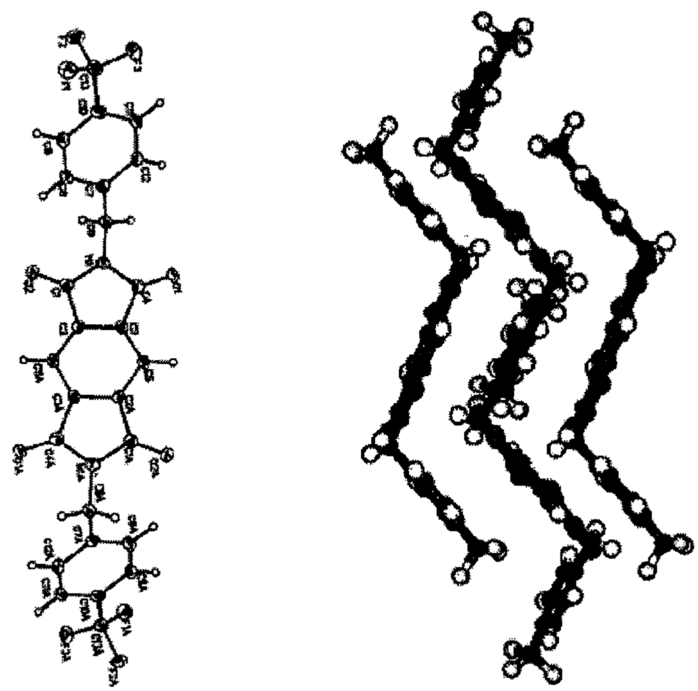
FIG. 3 shows crystal structure (left) and crystal packing diagram (right) of compound 1.

Single crystals of 1 were obtained by slowly cooling hot saturated DMF solutions. The unit cell of the single crystal is monoclinic with a=10.24 Å, b=11.53 Å, c=9.28 Å, α=90°, β=97.78°, γ=90°. The crystal structure and crystal packing diagram of 1 are shown in FIG. 3. Interestingly, the crystal structure of 1 exhibits a close π-π packing between the side chain benzene ring and the pyromellitic diimide core.

Example 2

N,N'-Di(4-(1H,1H,2H,2H-perfluorodecyl)benzyDpyromellitic diimide (2)

4-(1H,1H,2H,2H-Perfluorodecyl)benzylamine (0.553 g, 1.00 mmol) and pyromellitic dianhydride (0.10 g, 0.5 mmol) were dissolved in DMF (20 mL), then the mixture was stirred at 110° C. overnight. After cooling to ambient temperature, the mixture was filtered and washed with large amount of hot DMF (~50° C.), then with methanol, and a white solid (0.4 g, 62%) was obtained. The final yield is relatively low, because some amount of product dissolved in hot DMF. This crude product is insoluble in common solvents, and it was then purified by vacuum sublimation. Elemental analysis (calcd for C, 41.01; H,1.72; F, 50.13; N, 2.17; found: C, 41.08; H,1.61, F, 50.41; N, 2.21) indicates the high purity for final sublimed compounds. Mp: 282-283° C. MALDI-TOF/MS, m/z calcd for $C_{44}H_{22}F_{34}N_2O_4$: 1288, found: 1288.

Example 3

N,N'-Di(1H,1H,-perfluoropentyl)pyromellitic diimide (3)

1H,1H,-Perfluoropentylamine (2.74 g, 11.0 mmol) and pyromellitic dianhydride (1.09 g, 5.0 mmol) were dissolved in DMF (20 mL), then the mixture was stirred at 110° C. overnight. After cooling to ambient temperature, the mixture was filtered and washed with methanol, and a white solid (3.1 g, 91%) was obtained. Mp: 176-177° C. Elemental analysis: calcd for C, 35.31; H,0.89; F, 50.27; N, 4.12; found: C, 35.38; H,0.77, F, 50.44; N, 4.06. MALDI-TOF/MS, calcd for $C_{20}H_6F_{18}N_2O_4$: 680; found: 680. $^1$H NMR (400 MHz, $CDCl_3$, ppm): δ=4.45 (t, J=14.8 Hz, 4H), 8.46 (s, 2H).

A Linear Absorption spectrum for compound 3 is shown in FIG. 2 showing low absorption across the entire visible wavelength range.

Example 4

N,N'-Di(2-(4-trifluoromethylphenyl)ethyl)pyromellitic diimide (4)

2-(4-trifluoromethylphenyl)ethanamine (0.8 g, 4.2 mmol) and pyromellitic dianhydride (0.39 g, 1.8 mmol) were dissolved in DMF (20 mL), then the mixture was stirred at 110° C. overnight. After cooling to ambient temperature, the mixture was filtered and washed with methanol, and a white solid (0.95 g, 94%) was obtained.

Example 5

N,N'-Di(2-(perfluorophenyl)ethyl)pyromellitic diimide (5)

2-(perfluoropheny)ethanamine (1.35 g, 6.4 mmol) and pyromllitic dianhydride (0.53 g, 2.4 mmol) were dissolved in DMF (20 mL), then the mixture was stirred at 110° C. overnight. After cooling to ambient temperature, the mixture was filtered and washed with methanol, and a white solid (1.46 g, 98%) was obtained. Elemental analysis: calcd for C, 51.67; H,1.67; F, 31.44; N, 4.64; found: C, 51.84; H,1.62, F, 31.31; N, 4.81.

Example 6

N,N'-Di(2-(4-fluorophenyl)ethyl)pyromellitic diimide (6)

2-(4fluorophenyl)ethanamine (1.25 g, 9.0 mmol) and pyromellitic dianhydride (0.9 g, 4.1 mmol) were dissolved in DMF (20 mL), then the mixture was stirred at 110° C. overnight. After cooling to ambient temperature, the mixture was filtered and washed with methanol, and a white solid (1.8 g, 95%) was obtained.

Example 7

N,N'-Di(3,5-bis(trifluoromethyl)benzyl)pyromellitic diimide 3,5-bis(trifluoromethyl)benzyl amine (3.03 g, 12.5 mmol) and pyromellitic dianhydride (1.34 g, 6.1 mmol) were dissolved in DMF (20 mL), then the mixture was stirred at 110° C. overnight. After cooling to ambient temperature, the mixture was filtered and washed with methanol, and a white solid (3.6 g, 88%) was obtained. Elemental analysis: calcd for C, 50.32; H,1.81; F, 34.11; N, 4.19; found: C, 50.35; H,1.71, F, 34.37; N, 4.25.

Example 8

Devices

For exemplary devices, the semiconducting films were deposited at substrate temperatures of 25-115° C., with 300 nm-thick $SiO_2$ dielectrics, and evaporated gold top contact source and drain electrodes, as shown in FIG. 1. The thickness of semiconducting films and gold electrodes are fixed at 45 nm and 60 nm, respectively. Depositions took place under vacuum at pressures of $3\times10^{-6}$ to $6\times10^{-6}$ mbar. To optimize device properties, films were deposited onto oxide surfaces treated with vapor-deposited silane monolayers. Compounds for self-assembled monolayer surface treatment, octadecyltrimethoxysilane (OTS-SAM) (Aldrich) were used as received. OTS-SAM treatments were conducted by piranha ($3H_2SO_4$:$1H_2O_2$) cleaning of sonicated wafers, followed by placement in a crystallization dish with a small vessel containing the silane. The dish is covered in foil and placed in a vacuum oven for at least 6 h and then rinsed with toluene, isopropanol followed in oven at 90° C. for 30 mins. Untreated devices were fabricated directly onto the wafer after sonication and vacuum oven drying. Devices in vacuum were measured using keithley 4200-SCS Semiconductor Characterization System and in air using an Agilent 4155C semiconductor parameter analyzer with the ICS lite software.

Differential Scanning Calorimetry

Figure 4:
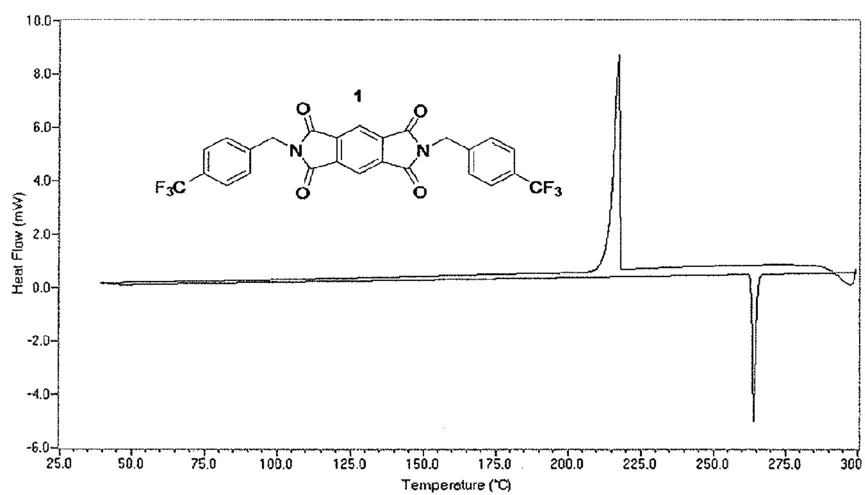
FIG. 4 shows a DSC thermogram of compound 1
Figure 5:
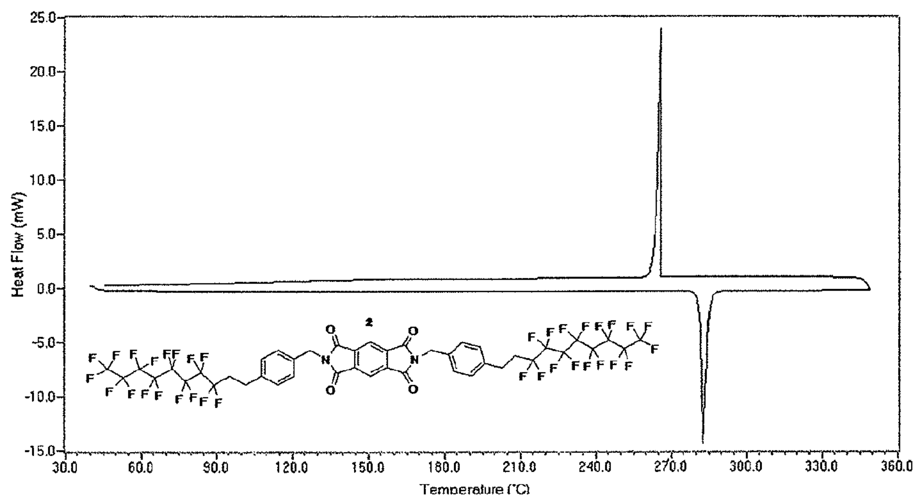
FIG. 5 shows a DSC thermogram of compound 2
Figure 6:
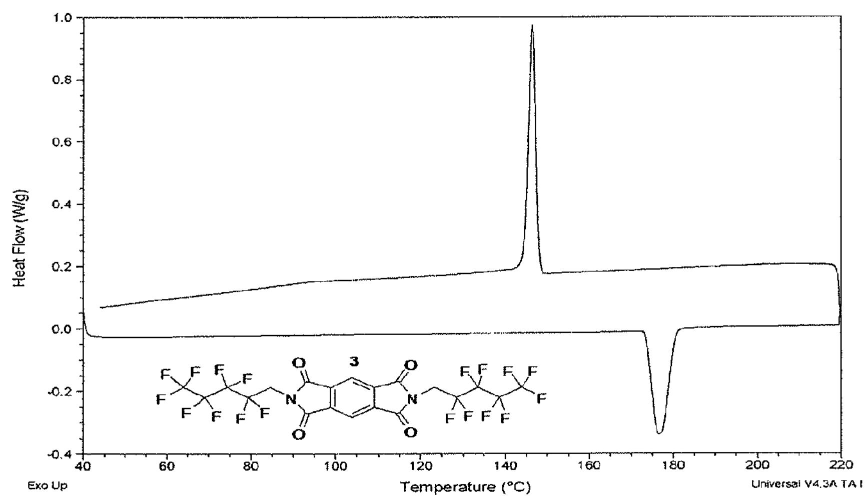
FIG. 6 shows a DSC thermogram of compound 3

Differential Scanning Calorimetry (DSC) thermograms of exemple compounds are shown in FIGS. 4-6.

Thin Film Crystallinity

X-ray Diffraction. X-ray diffraction scans were acquired in the Bragg-Brentano (θ-2θ) geometry using a Phillips X-pert Pro X-ray diffraction system. Scan parameters were: step size 0.02° and a time per step of 0.1 s. The beam wavelength was 1.5406 Å operated at 45 KeV and 40 mA.

Figures 7A, 7B, 7C:
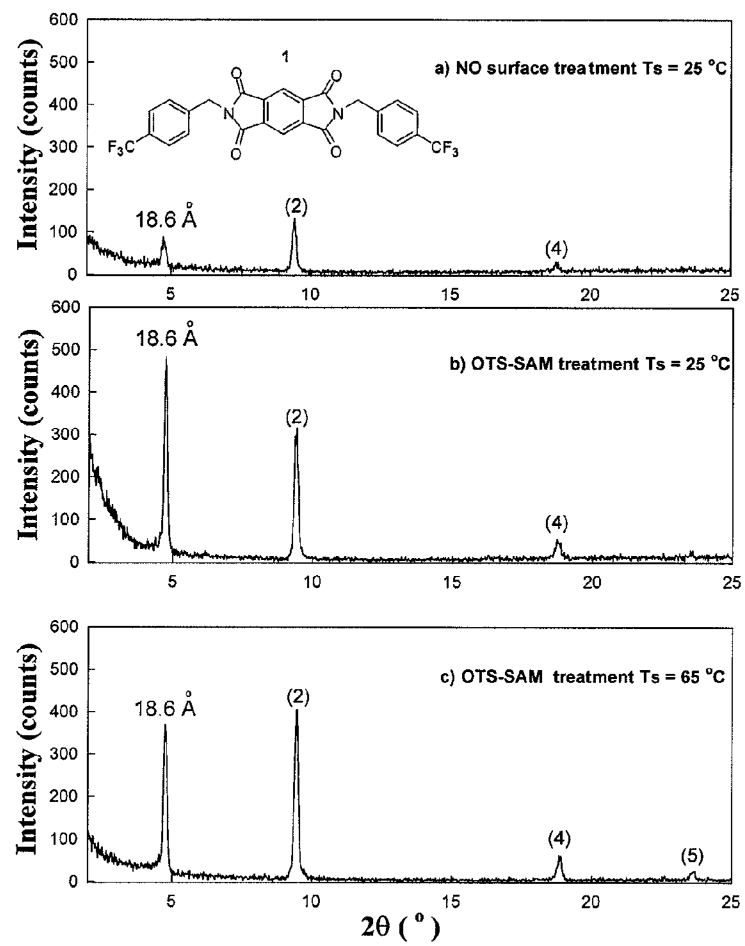
FIGS. 7A-7C show X-ray diffraction patterns of 1 deposited at 25° C. on an (a) untreated substrate, (b) OTS-SAM treated substrate, and (c) deposited at 65° C. on an OTS-SAM treated substrate.
Figure 8:
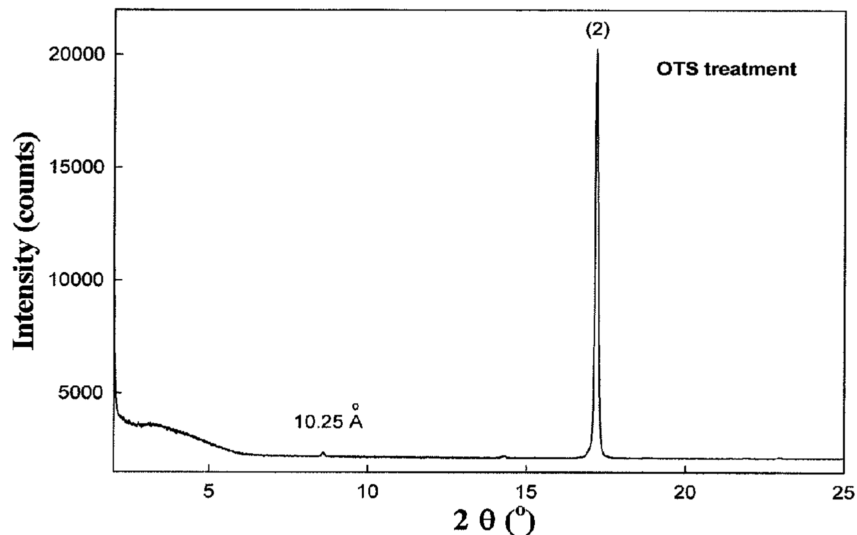
FIG. 8 shows an X-ray diffraction pattern of 1 deposited by solution process (2% DMF solution) on an OTS-SAM treated substrate.
Figure 9:
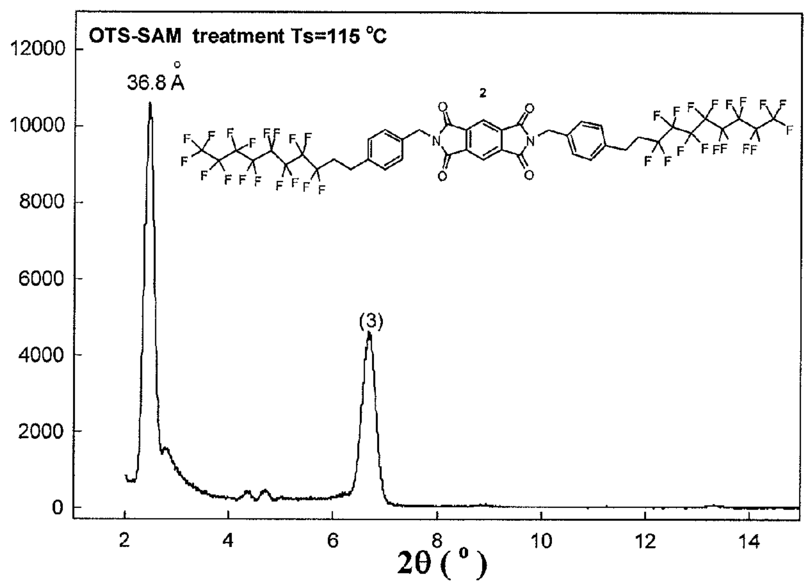
FIG. 9 shows an X-ray diffraction pattern of 2 deposited at 115° C. on an OTS-SAM treated substrate.
Figure 10:
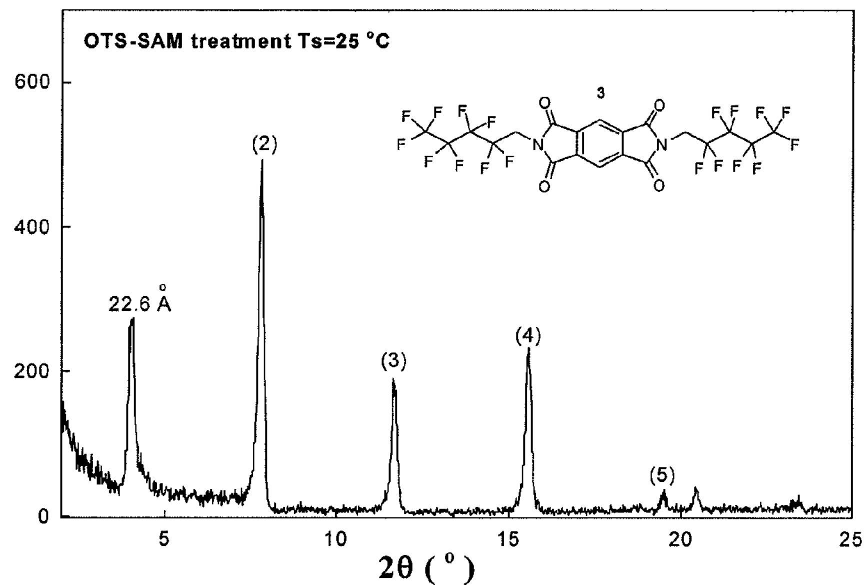
FIG. 10 shows an X-ray diffraction pattern of 3 deposited at 25° C. on an OTS-SAM treated substrate.

X-ray diffraction (XRD) spectra of the sublimed thin films for compounds 1, 2, and 3 (FIGS. 7-10) showed layer spacings of 18.6 Å, 36.8 Å, and 22.6 Å in that order, which is consistent with their molecular lengths. Molecules are believed to orient perpendicular to the substrate, though there is a modest degree of tilting. The 18.6 Å d-spacing observed for 1 reveals that the thin-film packing of 1 is different from its single crystal packing. For 1, several orders of the layer diffraction were observed for the samples with octadecyltrichlorosilane (OTS) surface treatment and deposited at 65° C., indicating its high crystallinity in thin film phase (FIG. 7).

Atomic Force Microscopy

Figure 11:
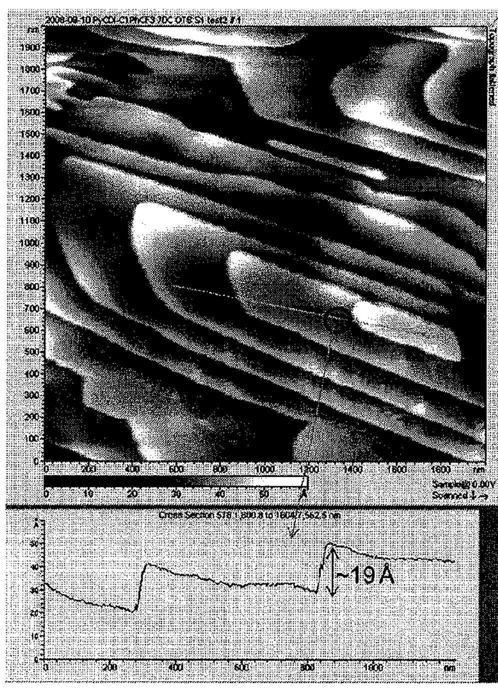
FIG. 11 shows AFM images of 1 deposited at 70° C. on an OTS-SAM treated substrate.
Figures 12A, 12B, 12C:
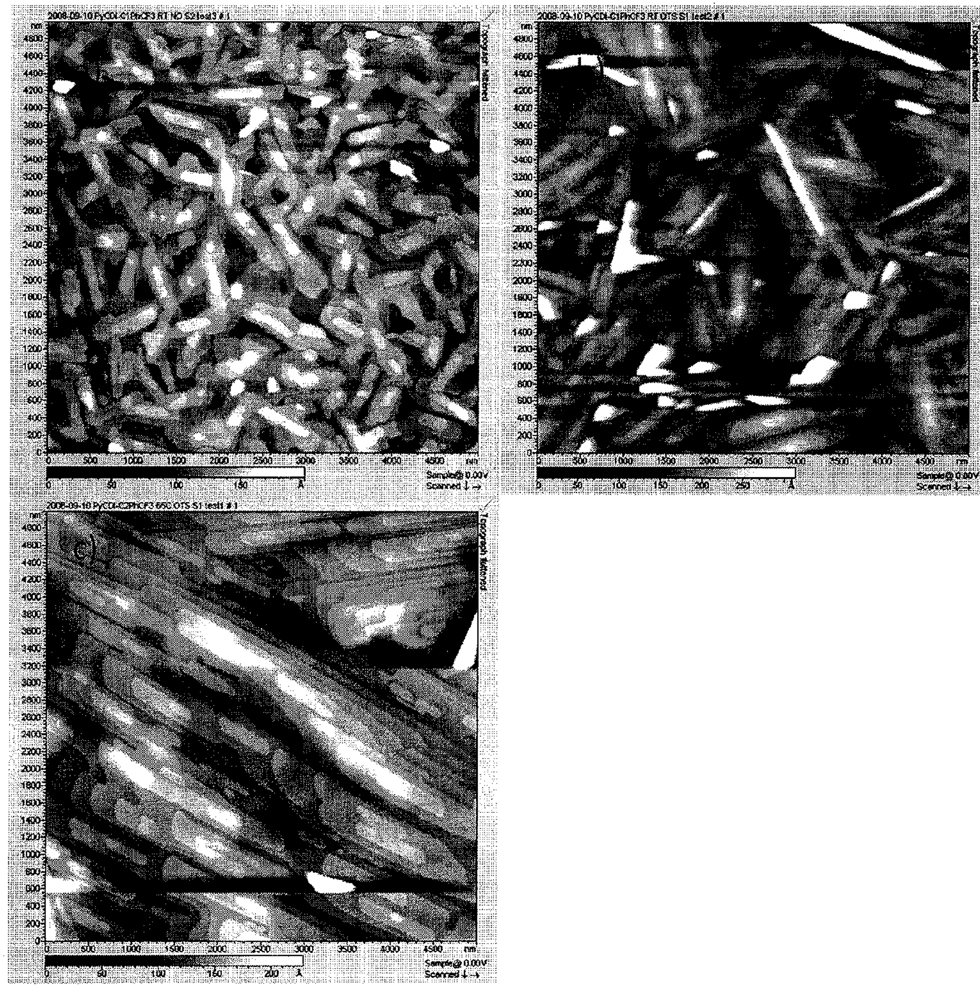
FIGS. 12A-12C show AFM images of 1 deposited at 25° C. on an (a) untreated substrate, (b) OTS-SAM treated substrate, and (c) deposited at 65° C. on an OTS-SAM treated substrate.

The morphology of films was observed by tapping mode AFM (Molecular Imaging PicoPlus). AFM images of compound 1 are shown in FIGS. 11 and 12. AFM images in FIG. 12 correlates the film morphology of compound 1 with the OTFT mobility. Mobility of compound 1 increases with increased substrate temperature and OTS surface treatment due to increased crystallinity and enlarged grain sizes.

Electrochemical Properties

Figure 13:
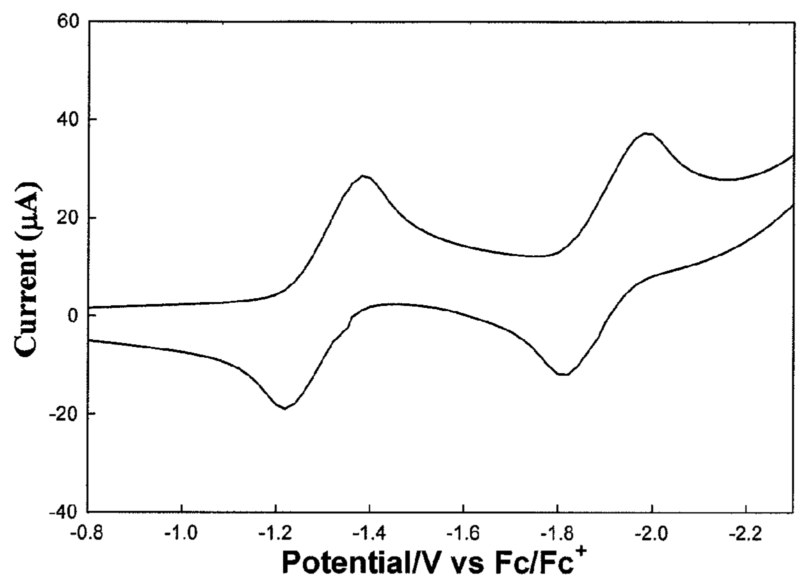
FIG. 13 provides CV Traces for compound 1.
Figure 14:
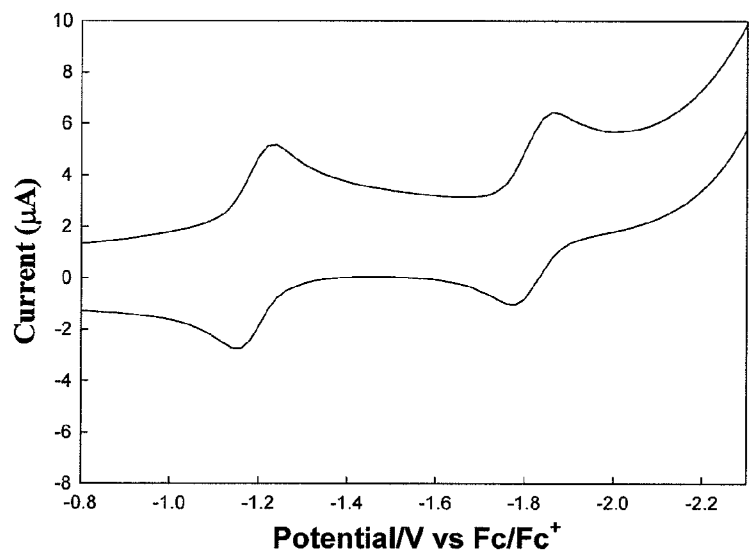
FIG. 14 provides CV Traces for compound 3.

The electrochemical properties of 1 and 3 were investigated by cyclic voltammetry. The voltammograms are shown in FIGS. 13 and 14, and their reduction potentials, lowest unoccupied molecular orbital (LUMO) levels (ca. 3.9 eV) are given in Table 1. Both 1 and 3 exhibit two reversible one-electron reductions, which are in agreement with reported observations for pyromellitic diimide derivatives. (Carroll et al., *Org. Lett.* 2003, 5, 3177)

TABLE 1

| Materials | $^1E_{1/2}$ | $^2E_{1/2}$ | $(E_{onset})_{red}$ | Experimental[a] LUMO (eV) | Theoretical[b] LUMO (eV) |
|---|---|---|---|---|---|
| 1 | −1.30 | −1.90 | −1.23 | −3.87 | −3.46 |
| 3 | −1.20 | −1.82 | −1.13 | −3.97 | −3.54 |

[a]The LUMO energies are given based on the assumption that the energy of SCE is 4.7 eV vs vacuum, and $Fc/Fc^+$ is +0.380 vs SCE (i.e., 5.1 eV relative to vacuum) (Thompson et al, *Macromolecules*, 2005, 38, 5359);

[b]B3LYP/3-21G optimized structure in gas phase.

Device Characterization

Devices in vacuum were measured using keithley 4200-SCS Semiconductor Characterization System and in air using an Agilent 4155C semiconductor parameter analyzer with the ICS lite software. The mobilities were measured in the saturation regime according to the following relationship:

$$(I_d)_{sat}=(W/2L)\mu C_i(V_g-V_{th})^2$$

where W and L are the channel widths (6.5 mm) and lengths (270 μm), respectively, and $C_i$ is the capacitance of the insulator (10 nF). μ is mobility, $V_{th}$ is the threshold voltage, and $V_g$ is the gate voltage. (S. M. Sze and K. K. Ng, Physics of semiconductor devices, Johns Wiley and sons: New York, 2006)

Table 2 lists a summary of device performance for 1 deposited under various conditions, and for 2, 3, 4, 5, and 6 under one condition. Electron mobilities were calculated from the saturation regime and fitted in the regions of highest slope.

TABLE 2

| Comps | Ts (° C.) | Substrate treatment | μ ($cm^2V^{-1}s^{-1}$) | Max μ($cm^2V^{-1}s^{-1}$) | $V_{th}$(V) | On/off | No. devices tested |
|---|---|---|---|---|---|---|---|
| 1 | 25 | OTS | 0.036 | 0.038 (0.025) | 18.1 (28.5) | $10^5$ ($10^3$) | 12 |
| 1 | 25 | N | 0.004 | 0.0045 | 18.6 | $10^4$ | 8 |
| 1 | 65 | OTS | 0.055 | 0.056 | 14.9 | $10^6$ | 4 |
| 1 | 65 | N | 0.029 | 0.030 | 29.2 | $10^6$ | 4 |
| 1 | 70 | OTS | 0.070 | 0.074 (0.039) | 22.4 (31.2) | $10^6$ ($10^5$) | 14 |
| 2 | 115 | OTS | 0.069 | 0.079 (0.054) | 14.4 (15.4) | $10^6$ ($10^4$) | 16 |
| 3 | 25 | OTS | 0.023 | 0.030 (0.013) | 13.7 (21.6) | $10^5$ ($10^5$) | 7 |
| 4 | 50 | OTS | 0.129 | 0.136 (0.078) | 11.3 (32.8) | $10^6$ ($10^3$) | 5 |
| 5 | 40 | OTS | 0.081 | 0.084 (0.071) | 17.5 (28.3) | $10^5$ ($10^3$) | 7 |
| 6 | 50 | OTS | 0.104 | 0.115 | 17.4 | $10^5$ | 4 |

Values in parenthesis are measured in air. Ts: substrate temperature. OTS: octadecyltrichlorosilane. N: no treatment. $V_{th}$: threshold voltage.

Figure 15:
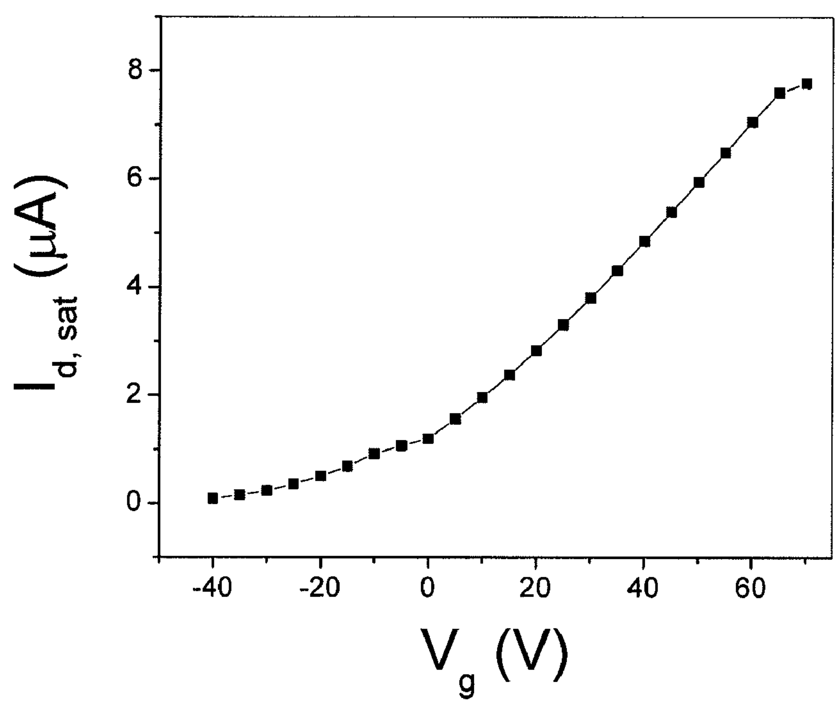
FIG. 15 provides Current-voltage characteristics of 4 prepared by solution process.

The results show that the charge carrier mobility for 1 increases when there is a self-assembled OTS thin layer between the gate dielectrics and organics. At the same time, mobility increases with increased substrate temperature due to increased crystallinity and enlarged grain sizes, which are confirmed by XRD spectroscopy and AFM images. The highest mobility for 1 is 0.074 $cm^2/(Vs)$ obtained from a device deposited at 70° C., and with OTS surface treatment. Compound 4 also has mobility>0.01 $cm^2/Vs$ when solution deposited (FIG. 15). Compound 4 dissolved in chlorobenzene (concentration: 1% by weight) was dropcast at the substrate temperature of 110° C. and then baked at 110° C. for 30 min. Then a 100 nm-thick gold film was deposited as top-contact source and drain electrodes with a channel length (L) and width (W) of 12 μm and 125 μm, respectively. For 4 we achieved a highest mobility of 0.136 $cm^2/(Vs)$ and on/off ratio of $10^6$, when deposited on the OTS-treated surface at 50° C.

Figures 16A, 16B, 16C, 16D:
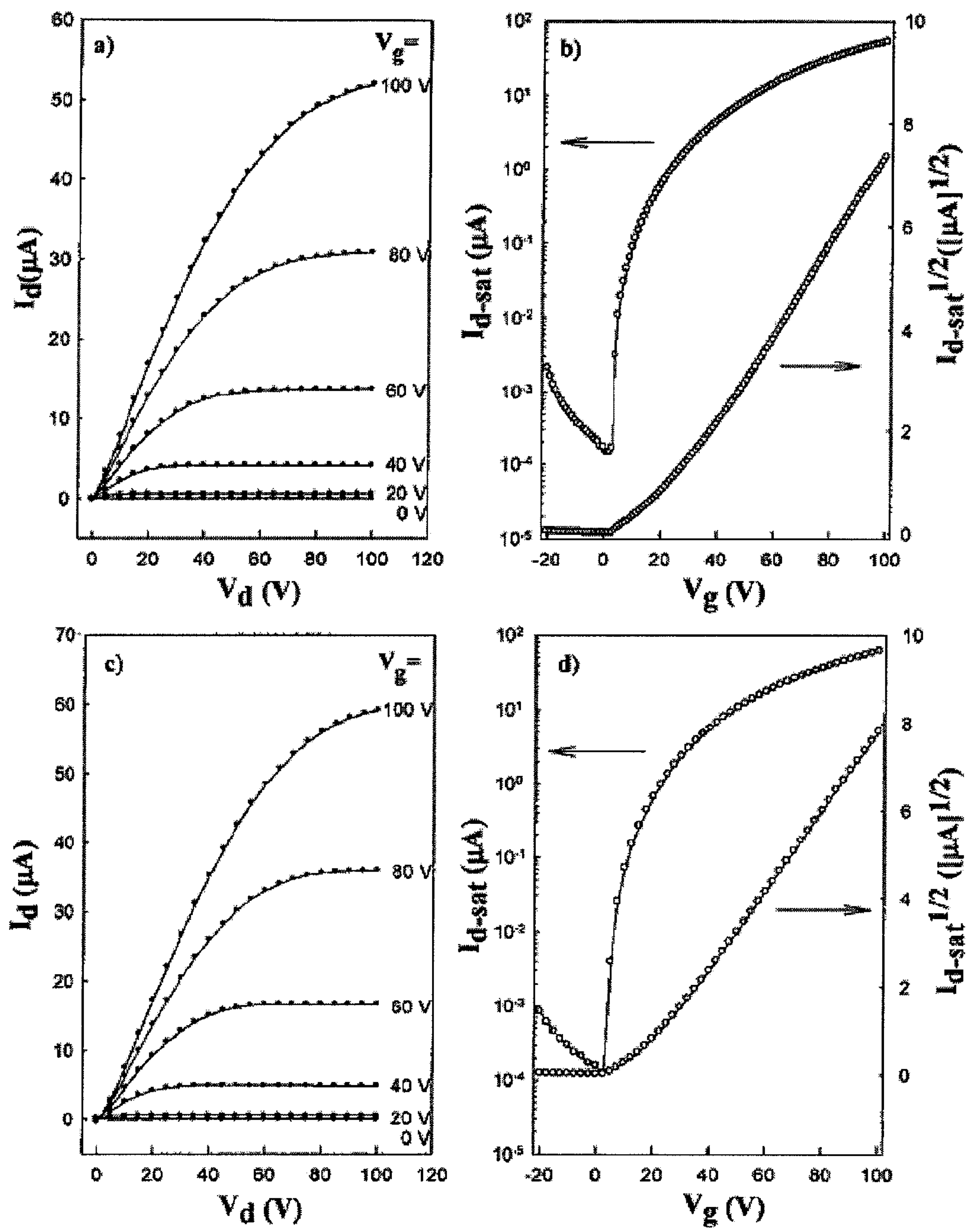
FIGS. 16A-16D provide Current-voltage characteristics of 1 and 2 prepared by sublimation at a substrate temperature of Td=70° C. and 115° C. respectively. a) a plot of Id versus Vd for compound 1; b) a plot of Id-sat versus Vg for compound 1; c) a plot of Id versus Vd for compound 2; d) a plot of Id-sat versus Vg for compound 2.

The measured current-voltage characteristics for all the devices show well-defined gate modulation. As an example, FIG. 16 depicts the current-voltage characteristics of 1 and 2 prepared by sublimation at substrate temperature of Ts=70° C. and 115° C. respectively. All obtained film effect transistors can be operated under ambient conditions in air, although their mobilities in air are not as high as those in vacuum. For example, the mobility and on/off ratio for 2 dropped to 0.054 $cm^2/(V.s)$ and $10^4$, respectively, due to the presence of water and oxygen. Values in vacuum and in air were obtained from devices which had been previously exposed to air for at least 15 mins and 30 mins, respectively. We did generally observe a decrease in mobilities when the devices were operated in air and an increase in mobilities when the devices were resumed being operated in vacuum.

In summary, a novel family of n-channel materials based on pyromellitic diimide derivatives have been synthesized and fabricated for organic field effect transistors. The field effect electron mobility of these materials is found to be as high as 0.136 $cm^2/(V.s)$. In addition, the on/off ratios of pyromellitic diimide based transistors can reach a high value of 1,000,000.With its shorter π-conjugation length, the pyromellitic diimides are relatively transparent to visible light compared to naphthalene or perylene tetracarboxylic diimides with the same side chain, which makes them promising candidates for transparent electronics.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. An n-channel organic semiconductor of Formula I:

Formula I

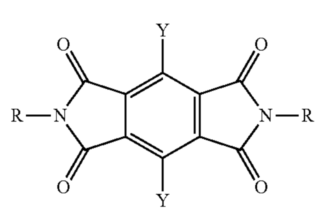

wherein Y is selected from the group consisting of hydrogen, A,

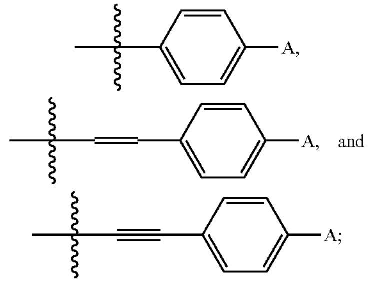

wherein A is an electron withdrawing substituent; and wherein R is selected from the group consisting of formulas III, IV, V and VI; and

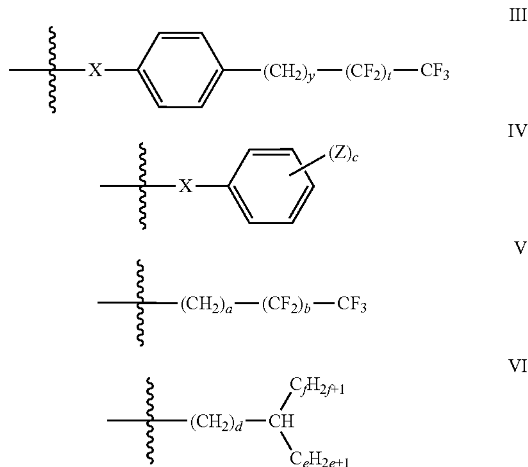

wherein X is —$(CH_2)_v$—, —$(CH_2)_w$—O—, or —$(CH_2)_w$—O—$(CH_2)_v$—; and wherein Z is —$OC_nF_{(2n+1)}$, or —$C_nF_{(2n+1)}$ where n is 1, 2, 3 or 4; and wherein a is independently 1, 2, 3, or 4; and wherein b is an integer from 1 to 20; and wherein c is 1, 2 or 3; and wherein d is independently 0, 1, 2, 3, or 4; and wherein e and f are independently integers from 2 to 12; and wherein v is independently 1, 2, 3, or 4, and w is independently 2, 3, or 4; and wherein y is each independently 0, 1, 2, 3, or 4; and wherein t is an integer from 1 to 20; or R is formula II

II

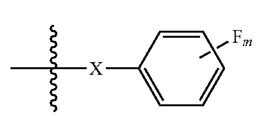

wherein X is —$(CH_2)_v$—, and wherein v is 2, 3, or 4; and 1 ; and wherein m is an integer from 1 to 5.

2. The n-channel organic semiconductor according to claim 1, wherein Y is hydrogen.

3. The n-channel organic semiconductor according to claim 2, selected from the group consisting of

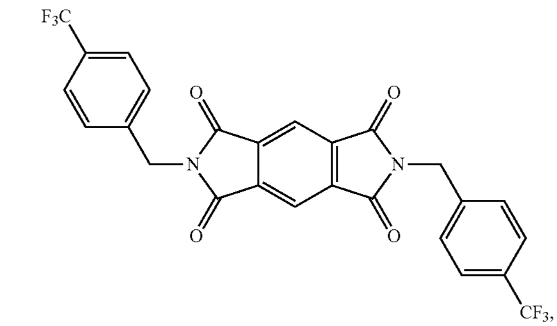

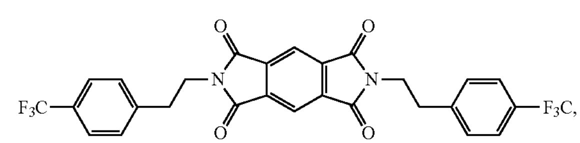

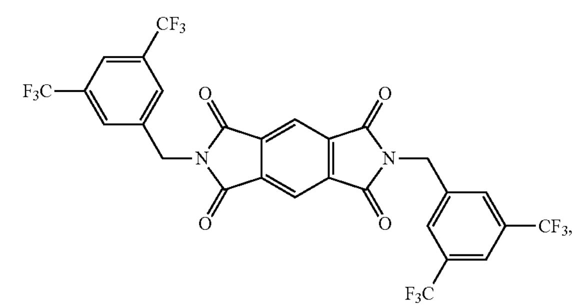

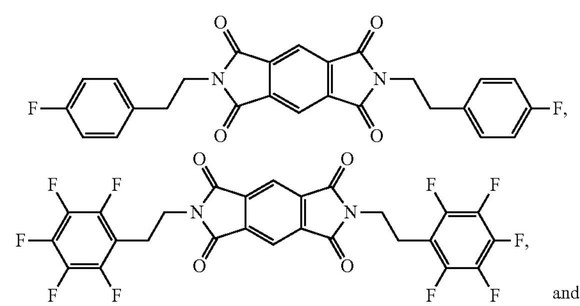

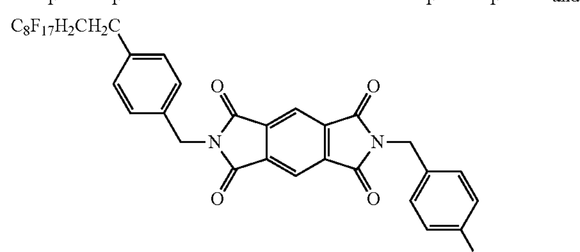

4. The n-channel organic semiconductor according to claim 1 wherein Y is not hydrogen and A is selected from the group consisting of halogen, fluorine, cyano, trifluoromethyl, petafluoroethyl, trifluoromethoxy, pentafluoroethoxy.

5. The n-channel organic semiconductor according to claim 4, selected from the group consisting of

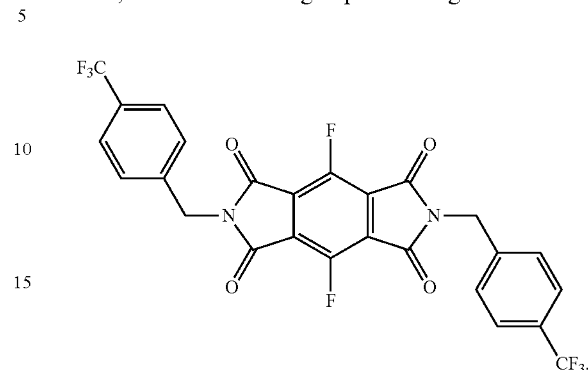

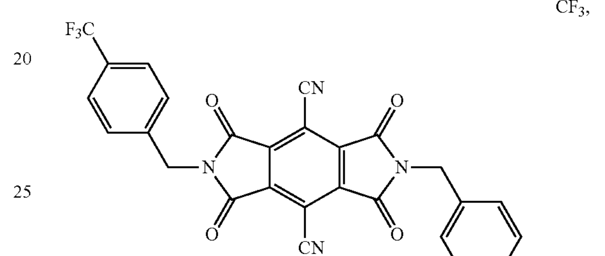

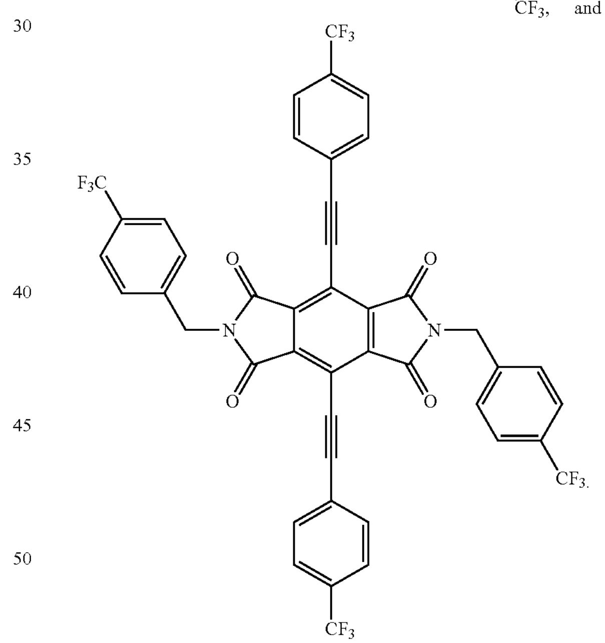

6. The n-channel organic semiconductor according claim 1 where R is

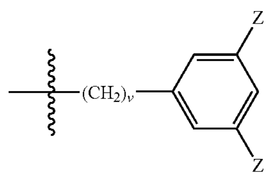

and wherein v is 1 or 2.

7. The n-channel organic semiconductor according to claim 1 where R is

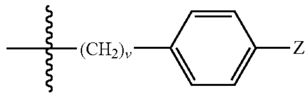

and wherein v is 1 or 2.

8. The n-channel organic semiconductor according claim 1 where R is

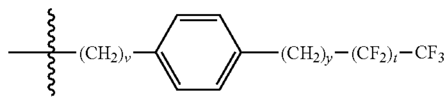

and wherein v is 1 or 2, y is 1 or 2, and t is 5, 6, 7, 8 or 9.

9. The n-channel organic semiconductor according to claim 1 where R is

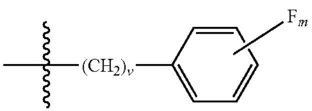

and wherein v is 2, and m is 1, 2, 3, 4, or 5.

10. The n-channel organic semiconductor according to claim 1, where R is

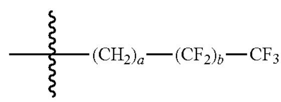

and wherein a is 1 or 2, and b is 5, 6, 7, 8, or 9.

11. The n-channel organic semiconductor according to claim 1 where R is

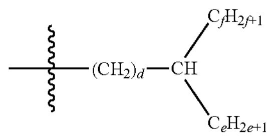

and wherein d is 0, 1 or 2, e is an integer from 2 to 12, and f is an integer from 2 to 12.

12. An electronic or electro-optic device comprising an n-channel organic semiconductor according to claim 1.

13. An electronic or electro-optic device comprising:

a first electrode;

a second electrode spaced apart from said first electrode; and an organic semiconductor layer arranged between said first and second electrodes wherein said organic semiconductor comprises an n-channel organic semiconductor of Formula I:

Formula I

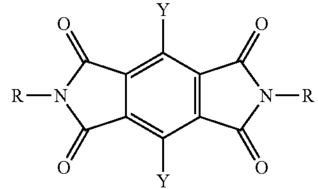

wherein Y is selected from the group consisting of hydrogen, A,

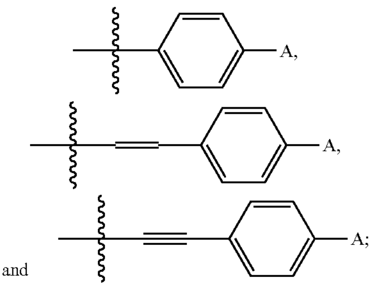

wherein A is an electron withdrawing substituent; and wherein R is selected from the group consisting of formulas III, IV, V and VI; and

III

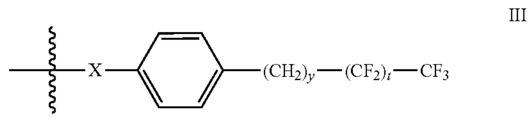

IV

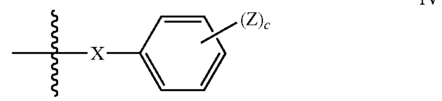

V

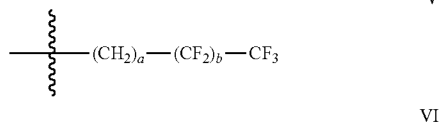

VI

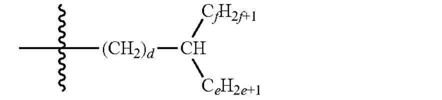

wherein X is —$(CH_2)_v$—, —$(CH_2)_w$—O—, or —$(CH_2)_w$—O—$(CH_2)_v$—; and wherein Z is —$OC_nF_{(2n+1)}$, or —$C_nF_{(2n+1)}$ where n is 1, 2 ,3 or 4; and wherein a is independently 1, 2, 3, or 4; and wherein b is an integer from 1 to 20; and wherein c is 1, 2 or 3; and wherein d is independently 0, 1, 2, 3, or 4; and wherein e and f are independently integers from 2 to 12; and wherein v is independently 1, 2, 3, or 4, and w is independently 2, 3, or 4; and wherein y is each independently 0, 1, 2, 3, or 4; and wherein t is an integer from 1 to 20; or R is formula II

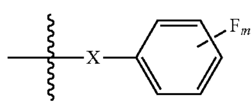

wherein X is —$(CH_2)_v$—, and wherein v is 2, 3, or 4; and 1; and wherein m is an integer from 1 to 5.

14. An electronic or electro-optic device according to claim 13, wherein Y is hydrogen.

15. An electronic or electro-optic device according to claim 14, said n-channel organic semiconductor selected from the group consisting of

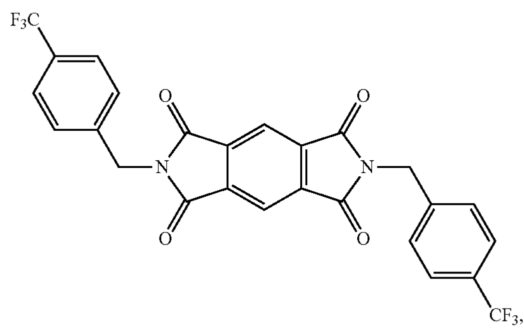

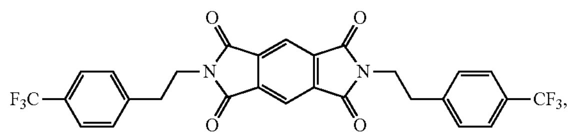

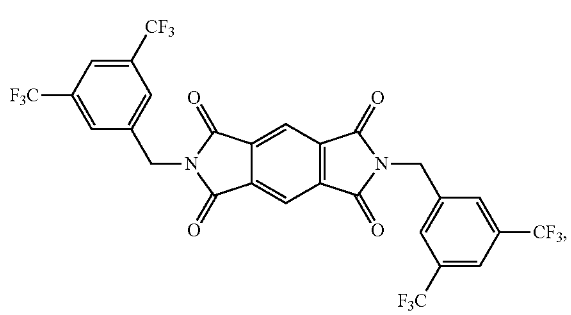

-continued

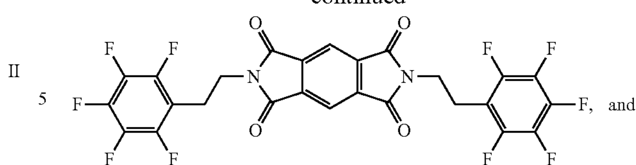

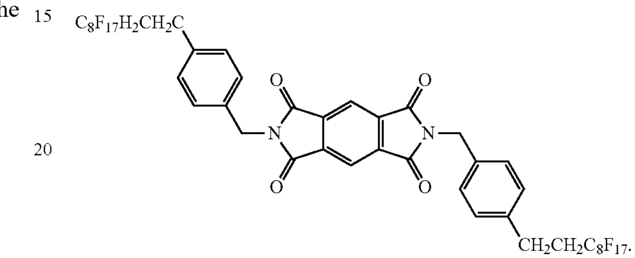

16. An electronic or electro-optic device according to claim 13, wherein Y is not hydrogen and A is selected from the group consisting of halogen, fluorine, cyano, trifluoromethyl, petafluoroethyl, trifluoromethoxy, pentafluoroethoxy.

17. An electronic or electro-optic device according to claim 16, said n-channel organic semiconductor selected from the group consisting of

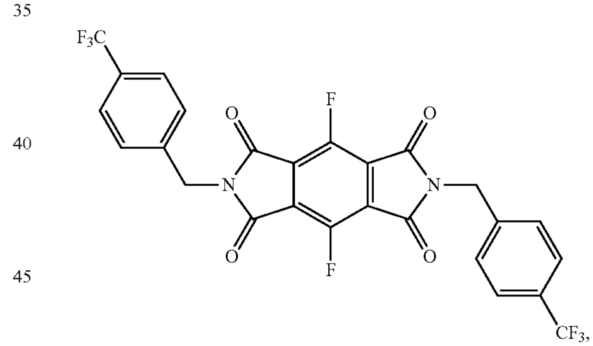

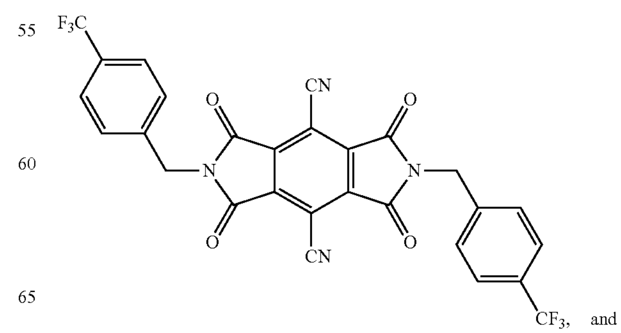

-continued

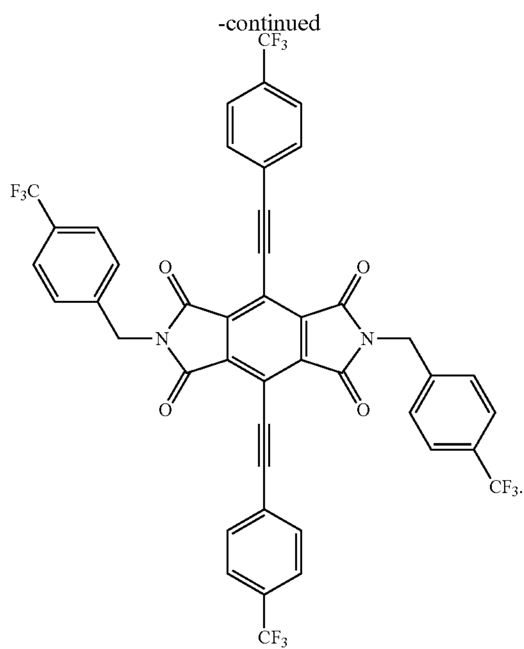

18. An electronic or electro-optic device according to claim 13, where R is

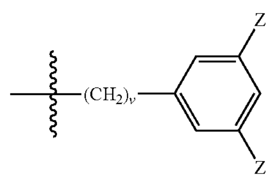

and wherein v is 1 or 2.

19. An electronic or electro-optic device according to claim 13, where R is

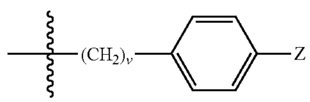

and wherein v is 1 or −2.

20. An electronic or electro-optic device according to claim 13, where R is

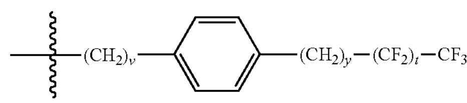

and wherein v is 1 or 2, y is 1 or 2, and t is 5, 6, 7, 8 or 9.

21. An electronic or electro-optic device according to claim 13, where R is

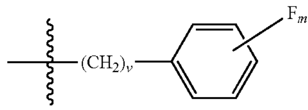

and wherein v is 2, and m is 1, 2, 3, 4, or 5.

22. An electronic or electro-optic device according to claim 13, where R is

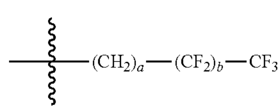

and wherein a is 1 or 2, and b is 5, 6, 7, 8, or 9.

23. An electronic or electro-optic device according to claim 13, where R is

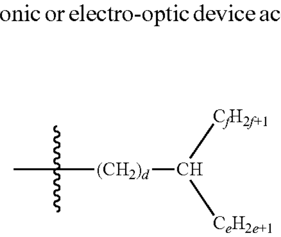

and wherein d is 0, 1 or 2, e is an integer from 2 to 12, and f is an integer from 2 to 12.

24. An electronic or electro-optic device according to claim 13, further comprising:

a dielectric layer formed on said second electrode between said semiconductor layer and said second electrode; and a third electrode spaced apart from said first and second electrodes, wherein said first electrode is a source electrode, said second electrode is a gate electrode and said third electrode is a drain electrode such that said electronic or electro-optic device is a field effect transistor.

25. An electronic or electro-optic device according to claim 24, wherein said field effect transistor has an on-off ratio of at least about $10^3$ in air.

26. An electronic or electro-optic device according to claim 24, further comprising a self assembled monolayer formed on said dielectric layer, wherein said self assembled monolayer enhances an electron mobility of said dielectric layer.

* * * * *